United States Patent [19]

Tsien et al.

[11] Patent Number: 5,049,673
[45] Date of Patent: Sep. 17, 1991

[54] FLUORESCENT INDICATOR DYES FOR CALCIUM WORKING AT LONG WAVELENGTHS

[75] Inventors: Roger Y. Tsien, Berkeley; Akwasi Minta, Albany, both of Calif.

[73] Assignee: Regents of the University of California, Berkeley, Calif.

[21] Appl. No.: 115,921

[22] Filed: Oct. 30, 1987

[51] Int. Cl.$^5$ ............... C07D 211/68; C07C 219/08; C07C 311/82; C07C 101/42; C07C 207/00
[52] U.S. Cl. .................. 546/107; 546/255; 546/256; 546/261; 546/265; 546/269; 546/272; 546/274; 546/285; 546/296; 546/300; 546/301; 546/302; 548/517; 548/518; 548/525; 548/527; 548/528; 548/541; 549/2; 549/21; 549/26; 549/27; 549/28; 549/59; 549/60; 549/65; 549/223; 549/225; 549/227; 549/415; 549/417; 549/472; 549/476; 260/351
[58] Field of Search ............... 549/223, 225, 227, 26, 549/27, 472, 476, 50, 60, 65, 21, 415, 417, 28, 2; 546/107, 265, 255, 256, 261, 269, 272, 274, 285, 296, 300, 301, 302; 562/403, 441; 260/351, 501.11, 501.13; 548/528, 517, 518, 525, 527, 541

[56] References Cited

U.S. PATENT DOCUMENTS

| | | | |
|---|---|---|---|
| 3,984,419 | 10/1976 | Hauck et al. | 548/528 |
| 4,318,846 | 3/1982 | Khanno et al. | 549/223 |
| 4,513,002 | 4/1985 | Aschwanden et al. | 548/528 |
| 4,543,402 | 9/1985 | Traynor | 548/541 |
| 4,585,785 | 4/1986 | Walsh et al. | 548/541 |
| 4,603,209 | 7/1986 | Tsien et al. | 548/236 |
| 4,686,432 | 8/1987 | Tsien et al. | 562/435 |

OTHER PUBLICATIONS

Adams, S. R., Kao, J. P. Y., and Tsien, R. Y., *J. Gen. Physiol.*, 88:99–109 (1986).
Grynkiewicz, G., Poenie, M., and Tsien, R. J., *J. Biol. Chem.*, 260:3440–3450 (1985).
Gurney, A. M., Tsien, R. Y., and Lester, H. A., *Proc. Natl. Acad. Sci. USA*, 84:3496–3506 (1987).
Tsien, R. Y., *Ann. Rev. Biophys. Bioeng.*, 12:91–116 (1983).
Tsien, R. Y., *Biochemistry*, 19:2396–2404 (1980).
Tsien, R. Y., and Poenie, M., *Trends Biochem Sci.*, 11:450–455 (1986).

*Primary Examiner*—Richard L. Raymond
*Assistant Examiner*—Raymond Covington
*Attorney, Agent, or Firm*—McCubbrey, Bartels, Meyer & Ward

[57] ABSTRACT

The present invention discloses a new class of calcium specific fluorescent indicator dyes having visible excitation and emission wavelengths. The new fluorescent indicator dyes combine at least one tricyclic chromophore with a tetracarboxylate parent $CA^{2+}$ chelating compound having the octacoordinate pattern of liganding groups characteristic of BAPTA to give a rhodamine-like or fluorescein-like fluorophore. Binding of $calcium^{2+}$ increases the fluorescence of the new compounds by up to 40-fold. The $calcium^{2+}$ dissociation constants are in the range 0.37–2.3 microM, so that the new indicators give better resolution of high $[CA^{2+}]$ levels than were previously obtainable with predecessor compounds such as quin-2 or fluo-2. The visible excitation wavelengths of the new compounds are more convenient for fluorescent microscopy and flow cytometry than the UV required by previous indicators.

11 Claims, 9 Drawing Sheets

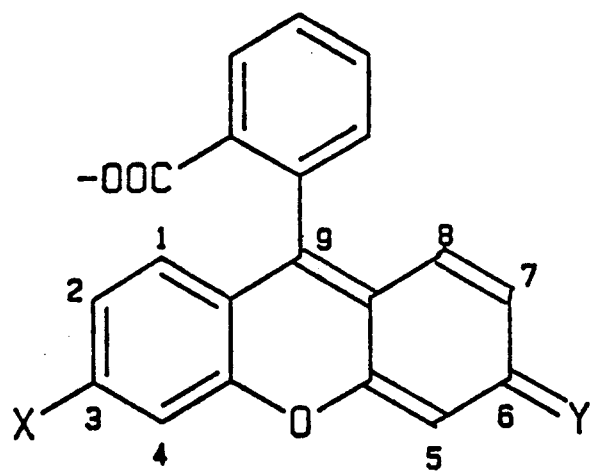
FIG. IA
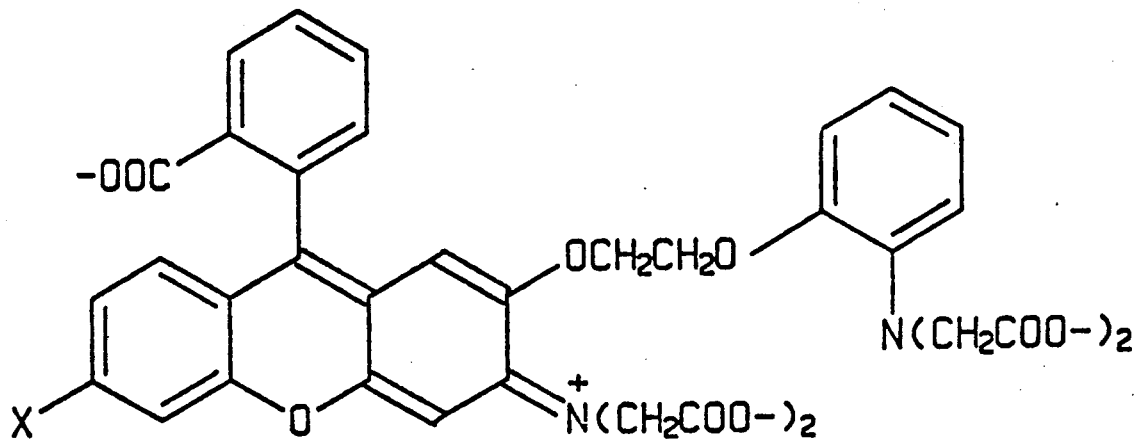
FIG. IB

FLUORESCENT INDICATOR DYES FOR CALCIUM WORKING AT LONG WAVELENGTHS

ACKNOWLEDGMENT

This invention was made with government support under grant numbers: GM-31004 and EY-04372 with the National Institutes of Health and the University of California. The United States government has certain rights in this invention.

FIELD OF THE INVENTION

The present invention relates to a new class of calcium specific fluorescent indicator dyes having visible excitation and emission wavelengths.

BACKGROUND OF THE INVENTION

Because of the importance of calcium as a intracellular messenger and regulator, a wide variety of techniques have been developed for measuring intracellular free calcium concentrations $[Ca^{2+}]_i$. The most successful of these techniques use dyes or proteins which change absorption or luminescence upon binding $Ca^{2+}$ ions. Currently the most popular of these methods is to monitor the fluorescence of BAPTA-like indicator dye compounds known as quin-2, fura-2, and indo-1. (See references 1–3 and U.S. Pat. No. 4,603,209.) The popularity of compounds such as quin-2, fura-2, and indo-1 stems from the following: (1) the ease with which these compounds can be loaded into cells by hydrolysis of membrane-permeant esters, and (2) the sensitivity and versatility of fluorescence, e.g., a mode of readout adaptable to bulk suspensions, flow cytometry, and microscopic imaging of single cells. Unfortunately, dyes such as quin-2, fura-2, and indo-1 all require excitation at ultraviolet wavelengths, near the cutoff point for transmission through glass. In addition, these wavelengths are potentially injurious to cells and tend to excite auto-fluorescence, for example, from the pyridine nucleotides. In addition, the UV range coincides with the wavelengths needed to photolyse chelators such as nitr-5 and nitr-7, to release their bound $Ca^{2+}$. (See references 4–6 and U.S. patent application Ser. No. 049,658, filed May 3, 1987, and U.S. Pat. No. 4,689,432, issued Aug. 25, 1987.) As a result, the existing indicators cannot readily be used to monitor release of "caged" $Ca^{2+}$ since the fluorescence excitation will begin to photolyse the buffer. Moreover, the absorbance of nitr-5 or nitr-7 and their photolysis reaction products may cause inner-filtering which can actually perturb the fluorescence excitation.

The problems discussed in the preceding paragraph would be avoided with $Ca^{2+}$ indicator dyes whose excitation wavelengths are in the visible or infrared range. There has been a long felt need for these dyes but previous attempts to produce such products resulted in disappointing fluorescent quantum efficiencies or $Ca^{2+}$ affinities (See reference 7.)

Fluorescein and rhodamine are fluorophores widely used in biology. Because of their ubiquity as labels in immunofluorescence and fluorescent analog cytochemistry (see reference 8), most fluorescence microscopes and flow cytometers are equipped to handle their wavelengths. As a result, it would be very useful if these highly fluorescent delocalized xanthenes could be combined with proven $Ca^{2+}$ specific binding sites of BAPTA or BAPTA-like compounds. Because of their similarity to fluoresceins and rhodamines, such new compounds would be optically compatible with almost any fluorometer or fluorescence microscope or flow cytometer now in use for immunofluorescent detection. Because of the ready availability of such immunofluorescent detection equipment, the new dyes would be welcomed by a number of biological investigators.

REFERENCE LIST

The present specification refers to the following publications, each of which is expressly incorporated by reference herein.

PUBLICATIONS

1. Adams, S. R., Kao, J. P. Y., Grynkiewicz, G. Minta, A., and Tsien, R. Y., *J. Am. Chem. Soc.*, 110(#10):3212–3220 (1988).
2. Adams, S. R., Kao, J. P. Y., and Tsien, R. Y., *J. Gen. Pysiol.*, 88:9a–10a (1986).
3. Bridges, J. W., *Standards in Fluorescense Spectrometry*, pp. 68–78, J.N. Miller, ed., Chapman and Hall, London (1981).
4. Drexhage, K. H., *Dye Lasers*, pp. 144–193, F. P. Schaefer, ed., Springer, New York (1973).
5. Ehrlich, P., and Benda, L., *Berichte der Deutsch, Chem. Gesell.*, 46:1931–1943 (1913).
6. Geisow, M. J., *Exp. Cell Res.*, 150:2–35 (1984).
7. Griffiths, J., *Colour and Constitution of Organic Molecules*, pp. 250–265, Academic Press, London (1976).
8. Grover, P. K., Shah, G. D., and Shah, R. C., *J. Chem. Soc. (Lond.)*, pp. 3982–3985 (1955).
9. Grynkiewicz, G., Poenie, M., and Tsien, R. Y., *J. Biol. Chem.*, 260:3440–3450 (1985).
10. Gurney, A. M., Tsien, R. Y., and Lester, H. A., *Proc. Natl. Acad. Sci. USA*, 84:3496–3500 (1987).
11. Kao, J. P. Y., and Tsien, R. Y., unpublished results.
12. Kurduker, R., and Subba Rao, N. V., *Proc. Indian Acad. Sci.*, A57:280–287, (1963).
13. Martell, A. E., and Smith, R. M., *Critical Stability Constants*, Vol. I, Plenum Press, New York (1974).
14. Martin, M. M., and Lindqvist, L., *J. Luminescence*, 10:381–390 (1975).
15. Parham, W. E., and Bradscher, C. K., *Acc. Chem. Res.*, 15:300–305 (1982).
16. Rink, T. J., and Pozzan, T., *Cell Calcium*, 6:133–144 (1985).
17. Taylor, D. L., and Wang, Y.-L., *Nature (Lond.)*, (284:405–410 (1980).
18. Tsien, R. Y., *Annu. Rev. Biophys. Bioeng.*, 12:91–116 (1983).
19. Tsien, R. Y., *Biochemistry*, 19:2396–2404 (1980).
20. Tsien, R. Y., and Poenie, M., *Trends Biochem. Sci.*, 11:450–455 (1986).
21. Tsien, R. Y., and Zucker, R. S., *Biophys. J.*, 50:843–853 (1986).
22. Von Braun, J., and Aust, E., *Berichte der Deutsch. Chem. Gesell.*, 49:989–999 (1913).
23. Wever, G., and Teale, F. W. J., *Trans. Faraday Soc.*, 53:646–655 (1957).

PATENTS

1. U.S. Pat. No. 4,603,209, issued July 29, 1986 to Tsien, et al. for "Fluorescent Indicator Dyes for Calcium Ions".

2. U.S. Pat. No. 4,689,432, issued Aug. 25, 1987 to Tsien, et al. for "Chelators Whose Affinity for Calcium is Decreased by Illumination".

BRIEF DESCRIPTION OF THE DRAWINGS

The drawings comprise six FIGURES, of which:

FIG. 1A shows the structure of rhodamines, rhodols, and fluoresceins;

FIG. 1B shows a possible design for a $Ca^{2+}$ indicator in which the chelating site directly includes a xanthene chromophore;

FIGS. 3-1 and 3-2 are synthetic pathways leading to rhod-2, fluor-2, and fluo-3;

DETAILED DESCRIPTION OF THE DRAWINGS

FIG. 1A. Structure of conventional rhodamines, rhodols, and fluoresceins. In a rhodamine, X would be a substituted amino group, $R^1R^2N-$, and Y would be similar but positively charged, $=N^+R^1R^2$. In a rhodol, X is as above, while Y becomes $=O$. In a fluorescein, X and Y are $-O-$ and $=O$ respectively.

FIG. 1B. A possible design for a $Ca^{2+}$ indicator in which the chelating site directly includes the xanthene chromopore. X would be $R^1R^2N-$ or $-O$.

Figures 1, 2:
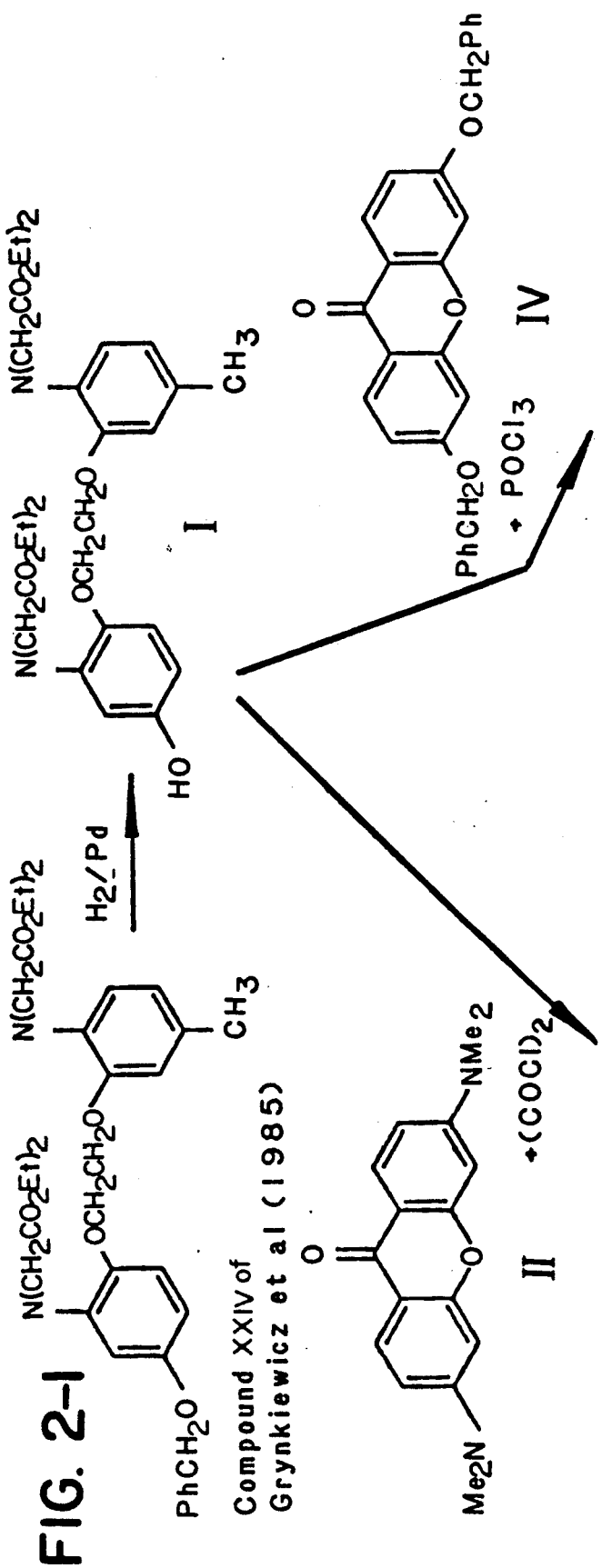
FIGS. 1-1 and 2-2 show a synthetic pathway leading to rhod-1 and fluo-1.
Figure 2:
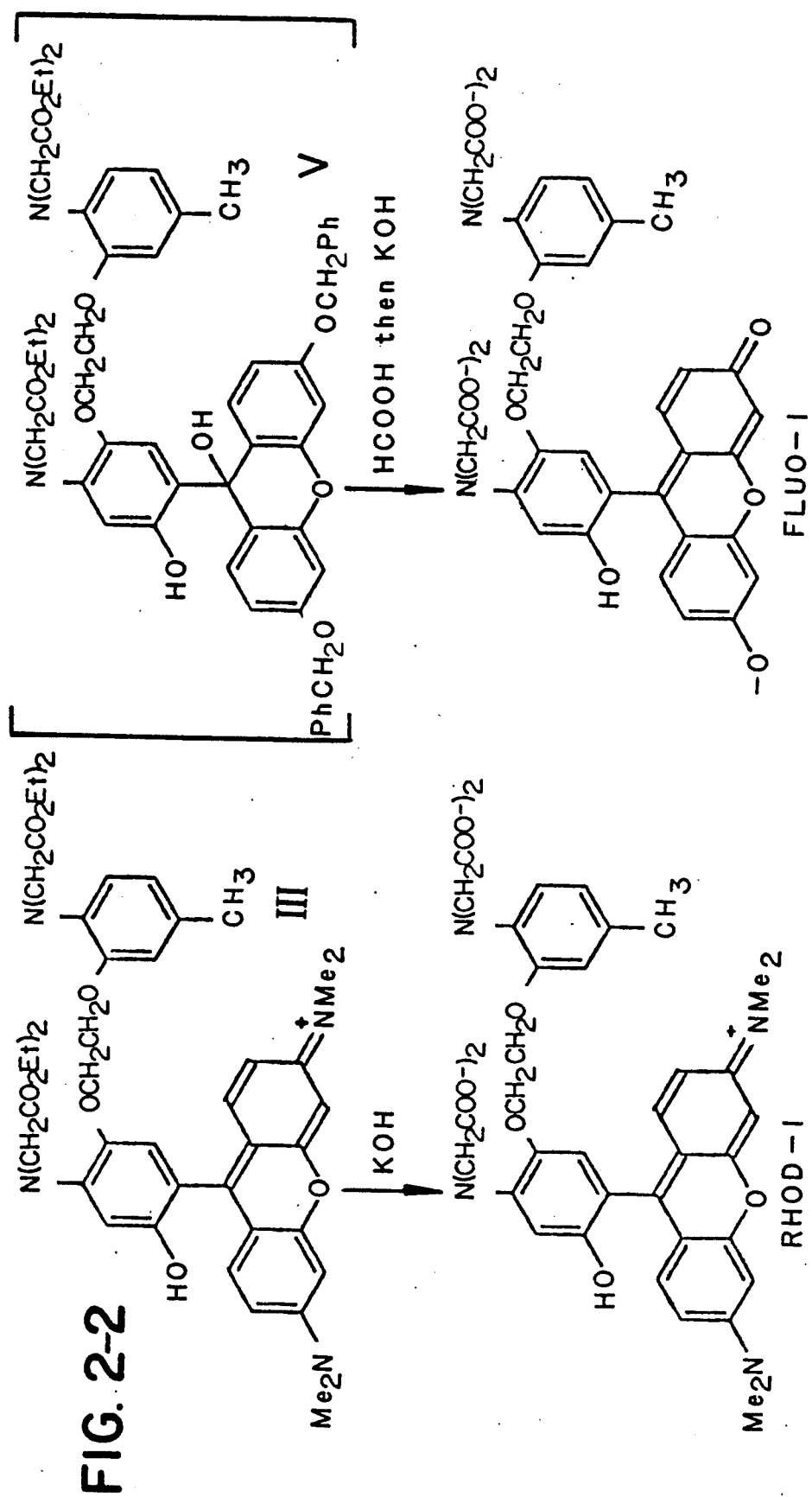

FIG. 2. Synthetic pathway leading to rhod-1 and fluo-1. Roman numerals are keyed to the synthetic details in the Experimental Procedures. Structures in brackets were used in situ without isolation.

Figures 1, 3:
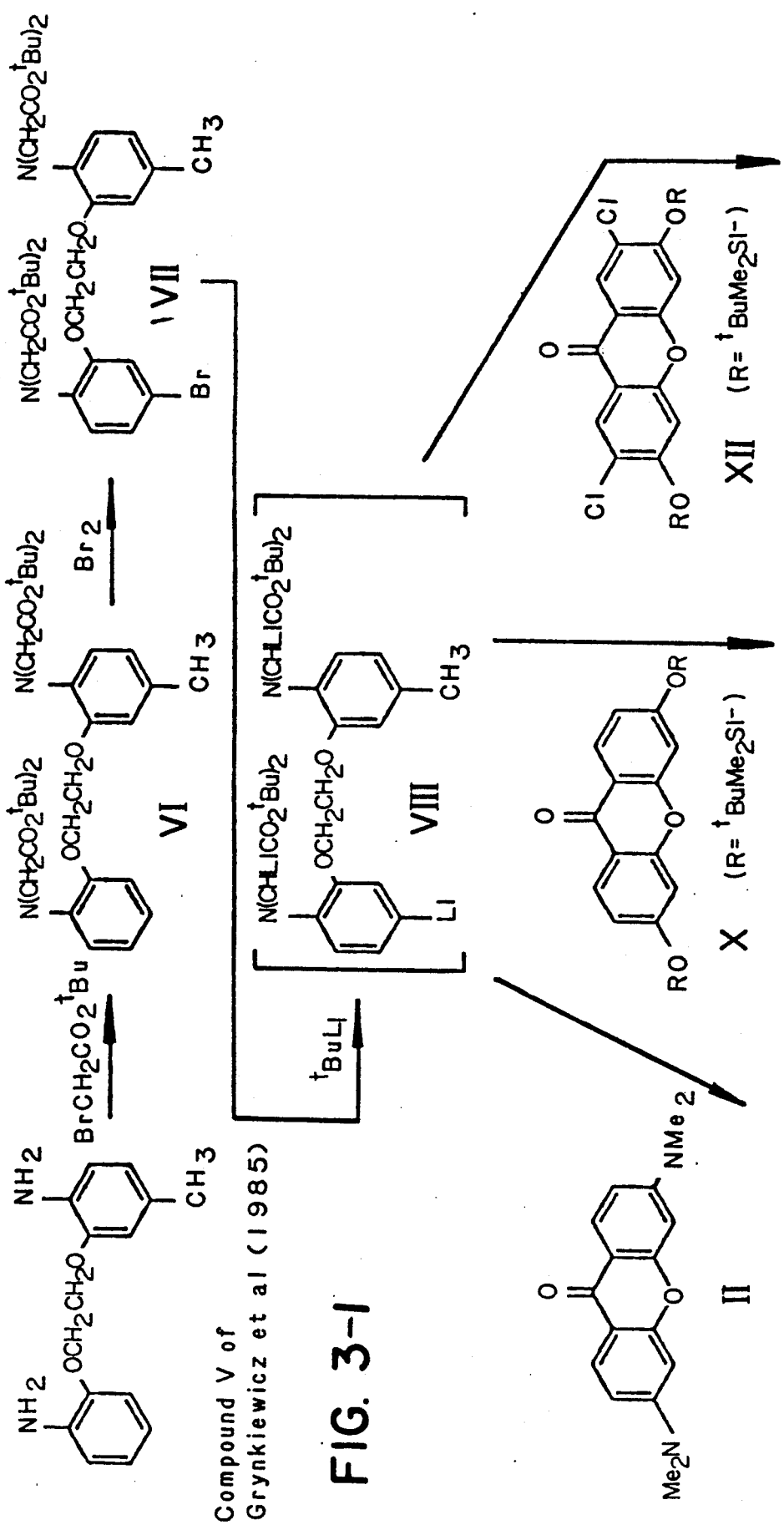
Figures 2, 3:
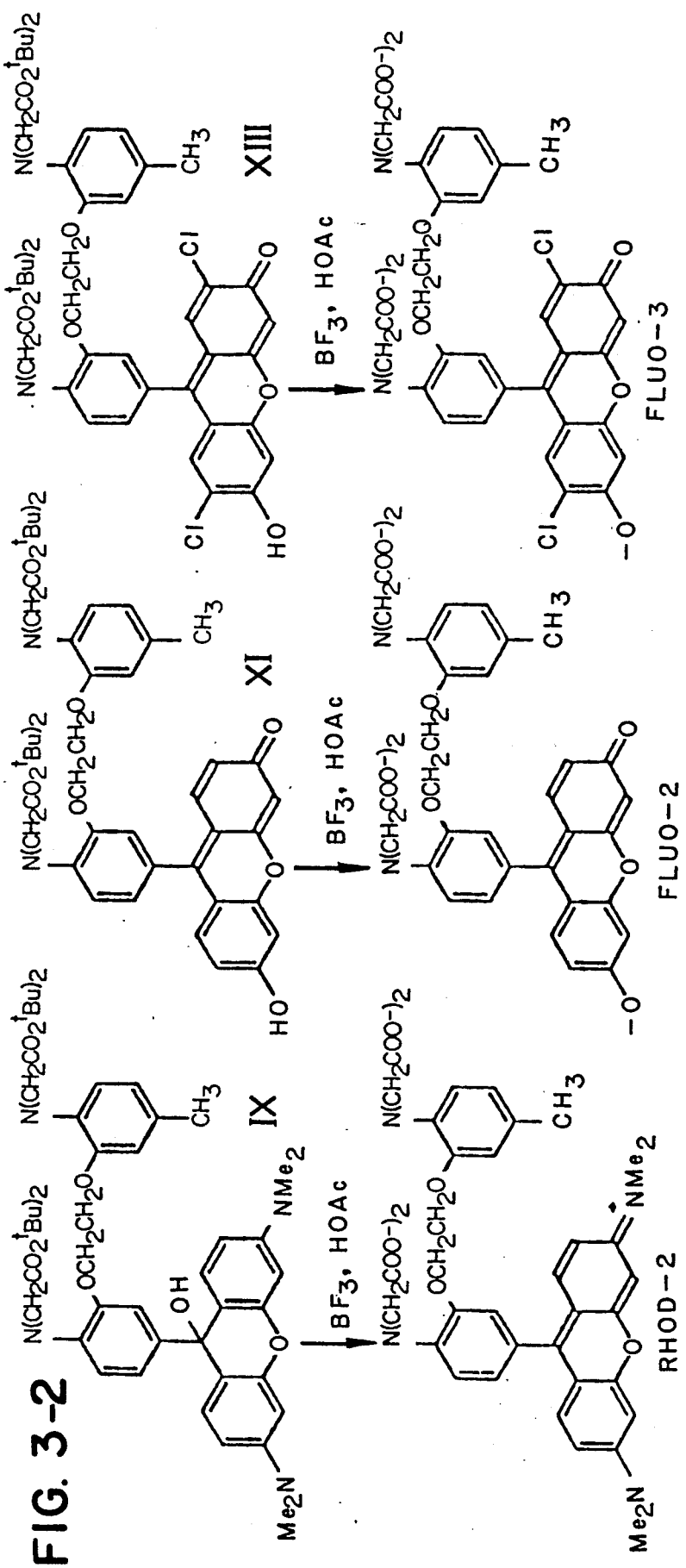

FIG. 3. Synthetic pathway leading to rhod-2, fluo-2, and fluo-3.

Figure 4A:
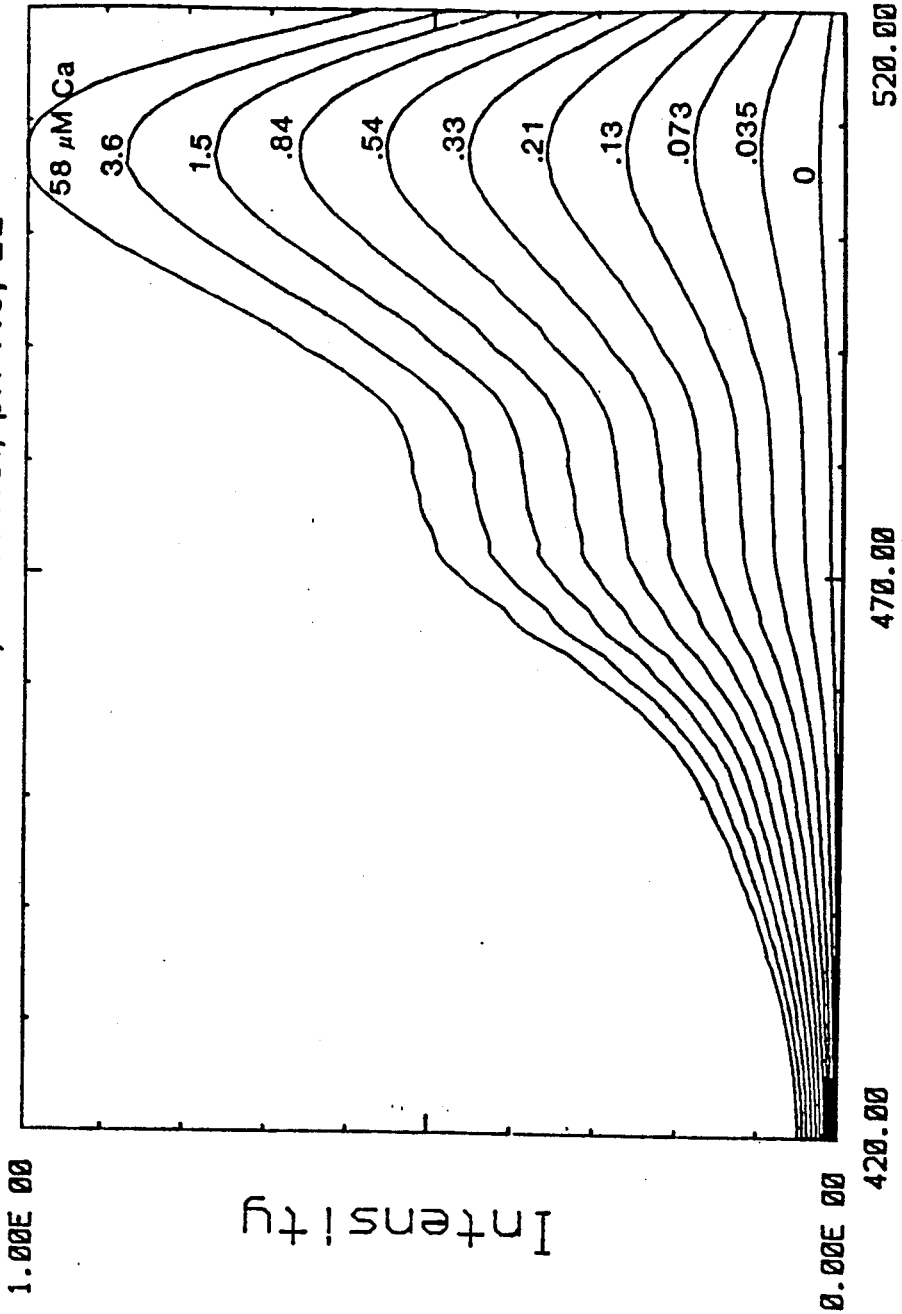
FIG. 4A shows the excitation spectra for fluo-3.
Figure 4B:
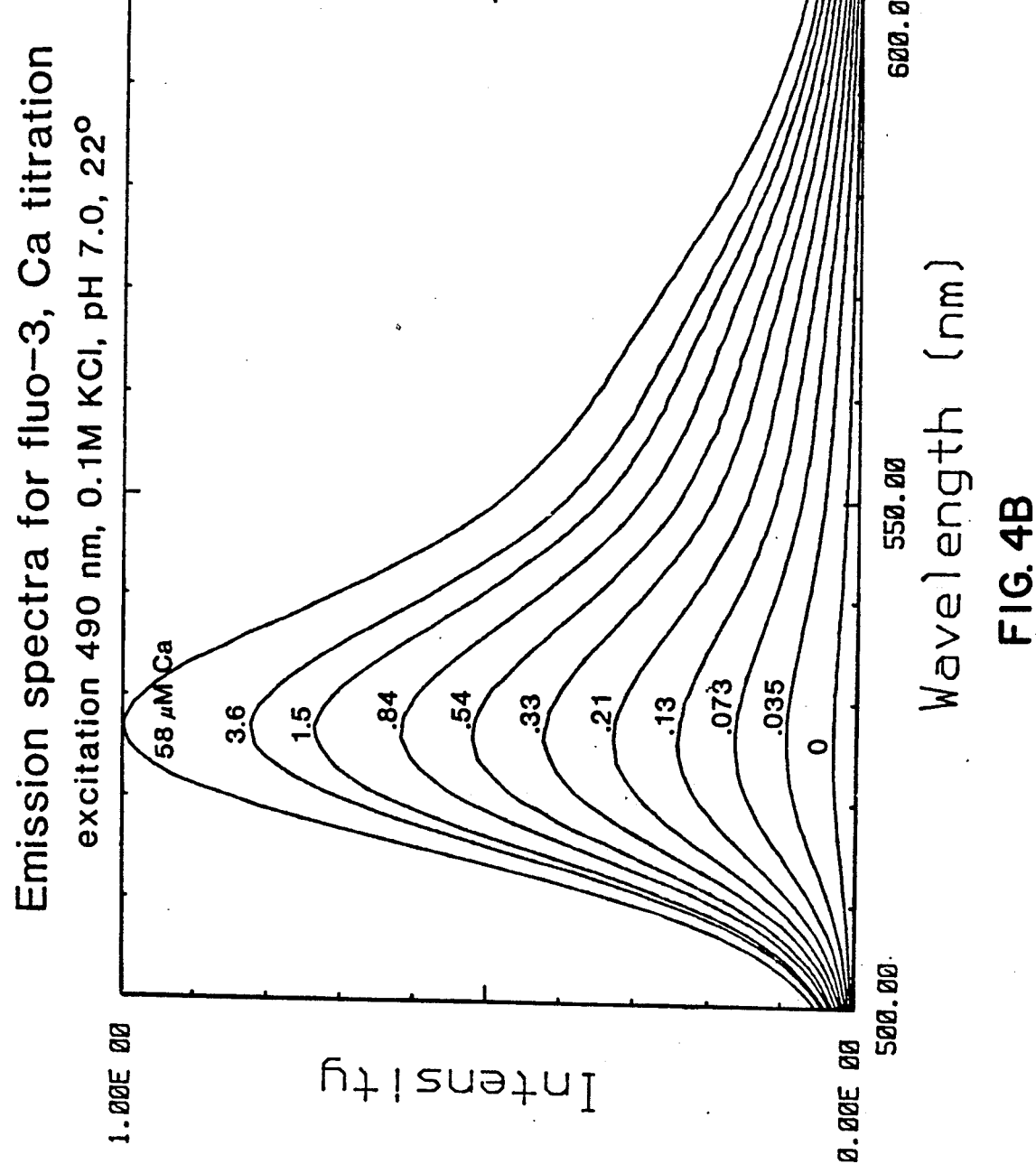
FIG. 4B shows the emission spectra for fluo-3.

FIG. 4. Excitation (A) and emission (B) spectra for fluo-3 at 22°±2° C. in buffers with free $Ca^{2+}$ values ranging from <1 nM to 58 microM. The titration was done starting with 3.5 ml of 100 mM KCl, 10 mM K-MOPS, 10 mM $K_2H_2$EGTA, 15 microM fluo-3, pH 7.03. The "O" Ca spectrum was recorded, then to reach n mM CaEGTA, (10-n) mM EGTA, n=1-10, aliquots of 3.5/(11-n) ml were iteratively discarded and replaced by equal volumes of 100 mM KCl, 10 mM K-MOPS, 10 mM $K_2$CaEGTA, 15 microM fluo-3, pH 7.0. After each iteration the pH (range 6.99 to 7.05) and spectra were recorded; each spectrum is labeled by the calculated free $Ca^{2+}$ in micromolar. The excitation and emission bandwidths were 1.9 nm and 4.6 nm respectively. All spectra have been normalized with respect to the peak of the 58 microM (n=10) curve. In A, emission was collected at 530 nm, and the excitation was corrected for lamp and monochromator characteristics using a rhodamine B quantum counter. In B, excitation was at 490 nm, and the emission spectrum is uncorrected for monochromator and detector sensitivity. The slightly low amplitude of the curve at 3.6 microM $[Ca^{2+}]$ is probably due to a small error in resetting the excitation monochromator to 490 nm.

Figure 5:
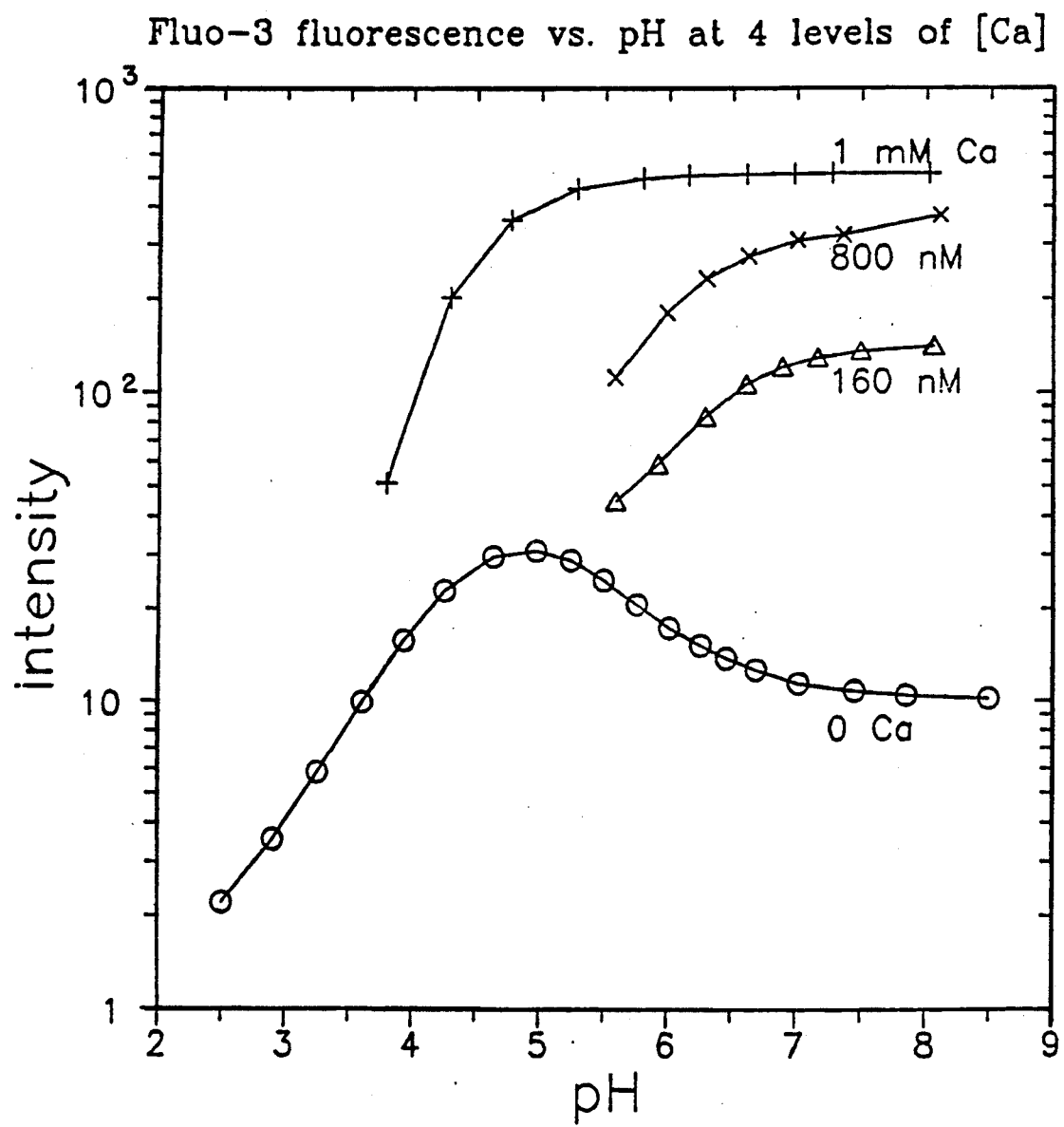
FIG. 5 is a graph showing fluorescence intensity of fluo-3 versus pH.

FIG. 5. Fluorescence intensity of fluo-3 (note log axis) vs. pH at 0, 160 nM, 800 nM, and 1 mM $[Ca^{2+}]$, 22°±2° C. All solutions contained 10 microM fluo-3, 100 mM KCl, and 10 mM Tris-MOPS, and were adjusted in pH with sufficiently concentrated $H_3PO_4$, HOAc, or KOH so as not to change the volume significantly during the titration. The "O Ca" points (open circles) were obtained with 5 mM EDTA and no added Ca; the "160 nM" (triangles) and "800 nM" (x) data were obtained with 5.2 mM dibromo-BAPTA. As explained in *Experimental Procedures*, the total $Ca^{2+}$ was increased from 0.25 to 0.47 mM to maintain free $[Ca^{2+}]$ at 160 nM as the pH was increased from 5.6 to 8.1; for 800 nM free $[Ca^{2+}]$, total $Ca^{2+}$ was 1.04 to 1.73 mM over the same pH range. The "1 mM ca" (+) points were obtained with 1 mM $CaCl_2$ and no phosphate (to avoid precipitation). The ordinate in arbitrary intensity units refers to the integral of the excitation spectrum from 420 to 520 nm with emission collected at 530 nm, 9 nm bandwidth. Because the spectra retained the same shape throughout the titration, integration was a convenient way of averaging and reducing each spectrum to a single intensity value.

Figure 6:
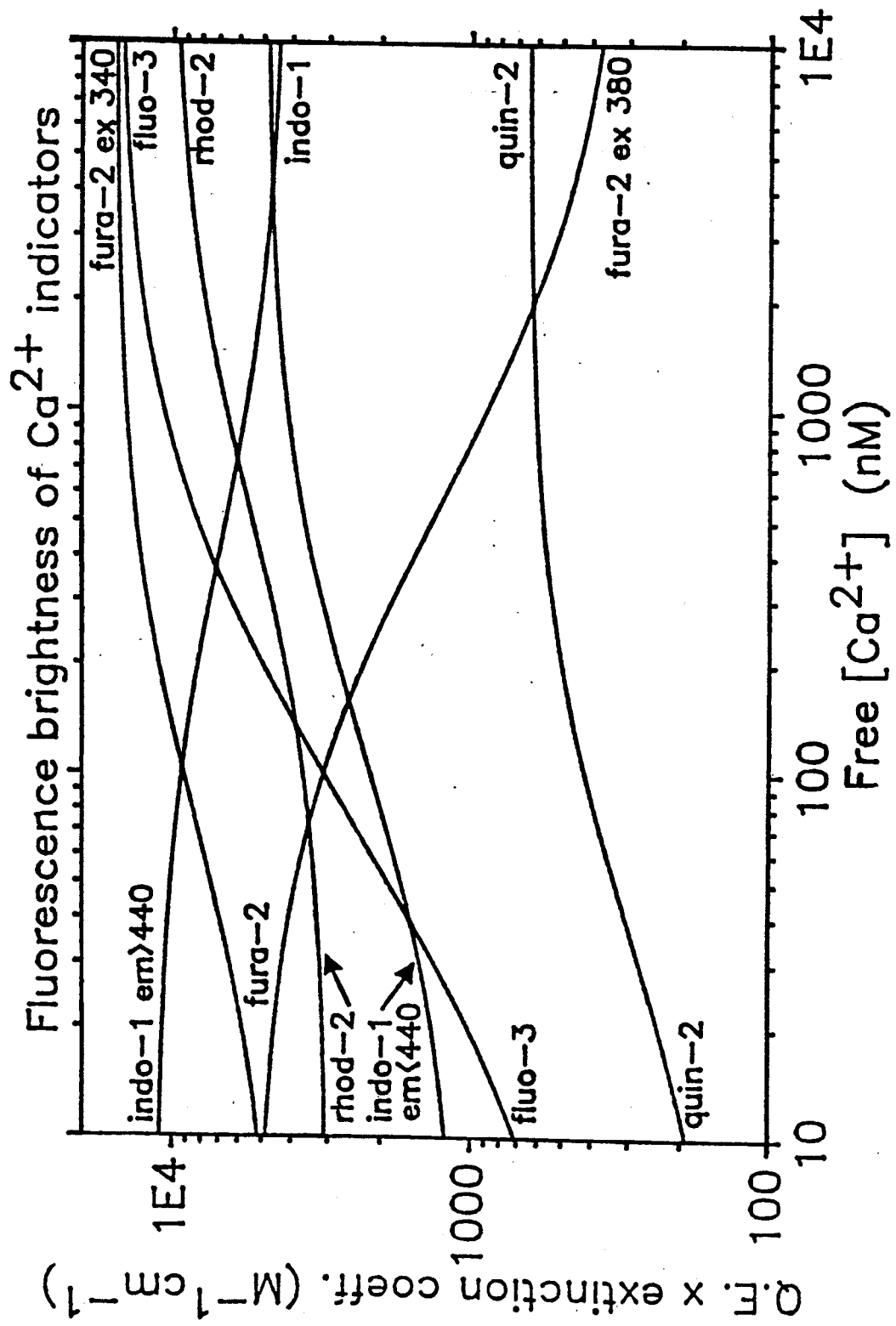
FIG. 6 is a graph showing the product of fluorescent quantum efficiency and excitation coefficient versus $Ca^{2+}$ for quin-2, fura-2, indo-1, rhod-2, and fluo-3.

FIG. 6. The product of fluorescence quantum efficiency and extinction coefficient vs. free $[Ca^{2+}]$ (note log axes for both) for quin-2, fura-2, indo-1, rhod-2, and fluo-3. All data are for room temperature, 0.1 M KCl, no added $Mg^{2+}$. The quin-2 curve was calculated for 339 nm excitation (extinction coefficient=$4.6\times10^3 M^{+1}cm^{-1}$ independent of $Ca^{2+}$) and quantum efficiency ranging from 0.029 to 0.14 with a $Ca^{2+}$ dissociation constant (Kd) of 78 nM (13). The "fura-2 ex 340" curve was calculated for 340 nm excitation (extinction coefficient(s)=$1.91\times10^4$ to $3.19\times10^4$) and quantum efficiency of 0.23 to 0.49 with a $K_d$ of 135 nM (2); the "fura-2 ex 380" curve was the same except based on extinction coefficient(s)=$2.25\times10^4$ to $6.25\times10^2$ for 380 nm excitation. Because indo-1 is usually employed for its emission rather than excitation shift, its curves were calculated for fixed 356 nm excitation (E=$3.25\times10^4$ to $1.63\times10^4$) and $K_d=250$ nM (2) but with the quantum efficiency (0.38 to 0.56) partitioned into emission components below 440 nm (0.033 to 0.30) and above 440 nm (0.347 to 0.26) for the two separate curves. The curve for fluo-3 used the data of Table I with extinction coefficients of $7.5\times10^4$ to $8.35\times10^4$ at 506 nm; the curve for rhod-2 assumed a $Ca^{2+}$-independent extinction coefficient of $1\times10^5$ $M^{-1}cm^{-1}$.

DEFINITIONS

In the present specification and claims, reference will be made to phrases and terms of art which are expressly defined for use herein as follows:

As used herein, "$[Ca^{2+}]i$" means intracellular free calcium.

As used herein, "EGTA" means ethylene glycol bis(-beta-aminoethyl ether)-N,N,N',N'-tetraacetic acid.

As used herein, "BAPTA" means 1,2-bis(2-aminophenoxy)ethane N,N,N',N'-tetraacetic acid; the chemical structure for BAPTA is:

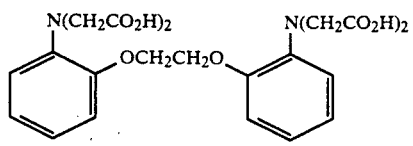

As used herein, "BAPTA-like means substituted derivatives of BAPTA which retain the essential characteristic of two bis(carboxymethyl)amino-substituted phenyl rings, said rings being linked at the positions ortho to the amines through a four atom bridge wherein the atom adjacent to each phenyl ring is N or O and the two center atoms are each C. By this definition, it is apparent that "BAPTA-like" includes compounds like quin-1 and quin-2.

As used herein, quin-1 means 2-[[2-bis(carboxymethyl)amino]-5-methylphenoxy]methyl]-8-bis(carboxymethyl)amino]-quinoline.

As used herein, quin-2 means 2-[[2-[bis(carboxymethyl)amino]-5-methylphenoxy]-6-methoxy-8-bis(carboxymethyl)amino]quinolline; the chemical structure for quin-2 is:

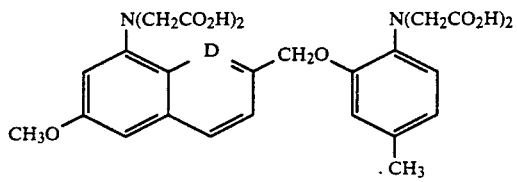

As used herein, "HEEDTA" means N-(2-hydroxyethyl)ethylenediamine-N,N',N'-triacetic acid.

As used herein, "NTA" means nitrilotriacetic acid.

As used herein, "MOPS" means 3-(N-morpholino)-propanesulfonic acid.

As used herein, pharmaceutically acceptable esters mean those readily hydrolyzable esters which are known and used in the pharmaceutical industry, especially alpha-acyloxyalkyl esters.

As used herein, pharmaceutically acceptable non-toxic salts mean carboxylic acid salts wherein the counterion or ions are all Na, K, NR$_4$+ (where R=H, C$_1$-C$_4$ alkyl or a mixture thereof), Ca, or Mg, or some combination of these counterions, or some combination of acid salts of these counterions plus free acid groups.

As used herein, microM means micromolar.

Temperatures herein are given in degrees centigrade.

For use herein, "dye" and "indicator" are used interchangeably.

As used herein, "xanthene" means tricyclic dibenzopyran, (CH$_2$(C$_6$H$_4$)$_2$O). Xanthene is the central heterocyclic nucleus of dyes such as fluorescein, eosin and rhodamine.

As used herein, "chromophore" means a chemical grouping which when present in an aromatic compound (the chromogen) gives color to the compound by causing a displacement of, or appearance of, absorbent bands in the visible spectrum.

As used herein, "tricyclic chromophore" means a chromophore having the tricyclic core structure, as shown below,

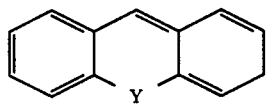

where y is defined as in Formula One, i.e., y is —O—, —NMe—, —S—, —CH$_2$—, —CMe$_2$—, —CF$_2$—. This tricyclic structure is the core of ring systems such as xanthene, acridine, thioxanthene, anthracene, anthrone, or fluorene.

As used herein, "fluorophore" means a fluorescent chromophore or a fluorescent tricyclic chromophore.

The chemical formulas for compounds shown in FIGS. 1 and 2 are identified with Roman numerals. These Roman numerals are used throughout the specification (see generally, the section labeled: METHODS OF SYNTHESIS) to identify compounds that correspond to those shown in the figures.

The new dyes disclosed herein are named with hyphens to distinguish the number 1 from the letter l, e.g., rhod-2, fluo-2, fluo-3, etc.

As used herein, rhod-1 means (9-(6-hydroxy-4-bis(-carboxymethyl)amino-3-(2-(2-bis(carboxymethyl)amino-5-methylphenoxy)ethoxy)phenyl)-6-dimethylamino-3H-xanthen-3-ylidene)dimethylammonium. The chemical structure for rhod-1 is shown in FIG. 2.

As used herein, rhod-2 means (9-(6-hydroxy-4-bis(-carboxymethyl)amino-3-(2-(2-(2-bis(carboxymethyl)amino-5-methylphenoxy)ethoxy)phenyl)-6-dimethylamino-3H-xanthen-3-ylidene)dimethylammonium. The chemical structure for rhod-2 is shown in FIG. 3.

As used herein, fluo-1 means 9-(6-hydroxy-4-bis(carboxymethyl)amino-3-(2-(2-bis(carboxymethyl)amino-5-methylphenoxy)ethoxy)phenyl)-6-hydroxy-3H-xanthen-3-one. The chemical structure for fluo-1 is shown in FIG. 2.

As used herein, fluo-2 means 9-(4-bis(carboxymethyl)amino-3-(2-(2-bis(carboxymethyl)amino-5-methylphenoxy)ethoxy)phenyl)-6-hydroxy-3H-xanthen-3-one. The chemical structure for fluo-2 is shown in FIG. 3.

As used herein, fluo-3 means 9-(4-bis(carboxymethyl)amino-3-(2-(2- bis(carboxymethyl)amino-5-methylphenoxy)ethoxy)phenyl)-2,7-dichloro-6-hydroxy-3 H-xanthen-3-one. The chemical structure for fluo-3 is shown in FIG. 3.

BRIEF DESCRIPTION OF THE INVENTION

The present invention comprises a new class of calcium specific fluorescent indicator dyes having visible excitation and emission wavelengths. The new fluorescent indicator dyes contain at least one tricyclic chromophore, such as a rhodamine or fluorescein fluorophore, coupled to a tetracarboxylate parent Ca$^{2+}$ chelating compound having the octacoordinate pattern of liganding groups characteristic of BAPTA. As in the "parental" EGTA or BAPTA-like compounds, the compounds of the present invention can have the two halves of the chelator joined by a simple linkage such as 1,2-ethanediyl (—CH$_2$CH$_2$—) or 1,2-propanediyl or 2,3-butanediyl; alternatively, in the compounds of the present invention, the stereochemical conformation of this simple linkage can be modified by adding bulky substituents or incorporating the simple linkage into a carbocyclic or heterocyclic ring.

In a first form, the new compounds are comprised of a single tricyclic chromophore coupled to a BAPTA-like Ca$^{2+}$ chelator wherein the two halves of the chelator are joined by a linkage selected from the group comprised of: (a) a 1,2-ethanediyl (—CH$_2$CH$_2$—) moiety, (b) a 1,2-propanediyl moiety, (c) a 2,3-butanediyl moiety, (d) a 1,2-cycloalkanediyl moiety, (e) two adjacent carbon atoms in a heterocyclic ring, for example a 3,4-tetrahydrofurandiyl, and (f) a 1,2-ethanediyl (—CH$_2$CH$_2$—) moiety having bulky substituents such as —C$_2$H$_5$, —CH$_2$OH, —COOH, or —CH$_2$COOH added thereto. In this form the new compounds are comprised of a chemical compound having the generic formula:

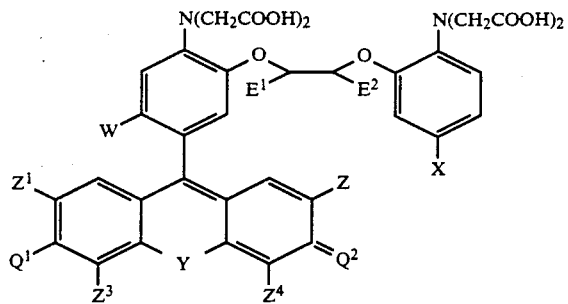

like $Ca^{2+}$ chelator wherein the two halves of the chelator are linked by a linkage selected from the group comprised of: (a) a 1,2-ethanediyl (—$CH_2CH_2$—) moiety, (b) a 1,2-propanediyl moiety, (c) a 2,3-butanediyl moiety, (d) a 1,2-cycloalkanediyl moiety, (e) two adjacent carbon atoms in a heterocyclic ring, for example a 3,4-tetrahydrofurandiyl, and (f) a 1,2-ethanediyl (—$CH_2CH_2$—) moiety having bulky substituents such as —$C_2H_5$, —$CH_2OH$, —COOH, or —$CH_2COOH$ added thereto. In this form the new compounds are comprised of a chemical compound having the generic formula:

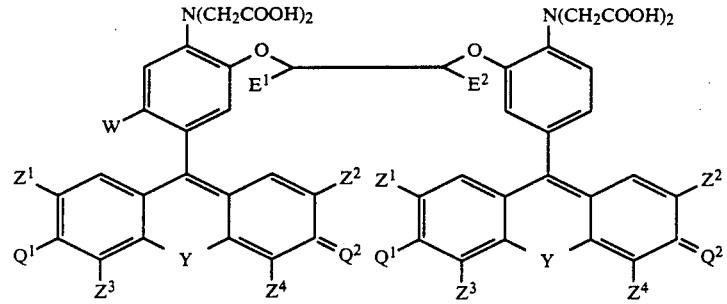

and the pharmaceutically acceptable nontox esters thereof wherein:

$E^1$ and $E^2$ are independently H, $CH_3$, $C_2H_5$, $CH_2OH$, COOH, or $CH_2COOH$, or $E^1$ and $E^2$ together are —$(CH_2)_m$—V—$(CH_2)_n$— where m and n are independently 1 or 2 and V is selected from the group consisting of —$CH_2$—, —O—, —NH—, —NMe—, —S—, and —S—S—;

W is H, OH, or COOH;

X is H, Me, COOH, F, Cl, Br, I, or $NO_2$;

Y is —O—, —NMe—, —S—, —$CH_2$—, —$CMe_2$—, —$CF_2$—,

or a direct sigma bond making a five-membered central ring;

$Z^1$, $Z^2$, $Z_3$, and $Z^4$ are independently H, F, Cl, Br, I, or Me, and $Q^1$, $Q^2$ equal $R^1R^2N-$,

or $HO-$, $O=$ or $R^1R^2N-$, $O=$, where $R^1$ and $R_2$ are independently selected from the group consisting of H, Me, and Et; or $Z^1$, $Q^1$, $Z^3$ together are

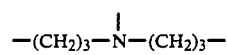

and $Z^2$, $Q^2$, $Z^4$ together are

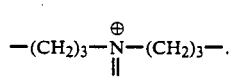

In a second form, the new compounds are comprised of two tricyclic chromophores coupled to a BAPTAand the pharmaceutically acceptable nontoxic salts and esters thereof wherein:

$E^1$ and $E^2$ are independently H, $CH_3$, $C_2H_5$, $CH_2OH$, COOH, or $CH_2COOH$, or $E^1$ and $E^2$ together are —$(CH_2)_m$—V—$(CH_2)_n$— where m and n are independently 1 or 2 and V is selected from the group consisting of —$CH_2$—, —O—, —NH—, —NMe—, —S—, and —S—S—;

W is H, OH, or COOH;

X is H, Me, COOH, F, Cl, Br, I, or $NO_2$;

Y is —O—, —NMe—, —S—, —$CH_2$—, —$CMe_2$—, —$CF_2$—,

or a direct sigma bond making a five-membered central ring;

$Z^1$, $Z^2$, $Z^3$, and $Z^4$ are independent H, F, Cl, Br, I, or Me, and $Q^1$, $Q^2$ equal $R_1R_2N-$,

or $HO^-$, $O=$ or $R^1R^2N$, $O=$, where $R^1$ and $R_2$ are independently selected from the group consisting of H, Me, and Et; or $Z^1$, $Q^1$, $Z^3$ together are

—$(CH_2)_3$—N—$(CH_2)_3$— and $Z^2$, $Q^2$, $Z^4$ together are

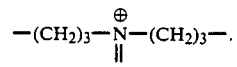

DETAILED DESCRIPTION OF THE INVENTION

The present invention comprises a new class of calcium specific fluorescent indicator dyes having visible excitation and emission wavelengths. Generic formulas for these calcium specific fluorescent dyes are given above. Compounds of the kind disclosed and claimed herein consist of at least one tricyclic chromophore joined to a calcium$^{2+}$ chelating portion containing two 2-bis(carboxymethyl) aminophenoxy groups linked through a simple 1,2-ethanediyl ($-CH_2CH_2-$), a 1,2-propanediyl, a 2,3-butanediyl, a 1,2-cycloalkanediyl, or two adjacent carbon atoms in a heterocyclic ring, for example a 3,4-tetrahydrofurandiyl.

In creating our new compounds we took into account the fact that the fluorophores most widely used in biology are probably those of fluorescein and rhodamine (see FIG. 1A). Because of their ubiquity as labels in immunofluorescence and fluorescent analog cytochemistry (see ref. 8), practically all fluorescence microscopes and flow cytometers are equipped to handle their wavelengths. It was therefore of interest to try to join these highly fluorescent delocalized xanthenes to the proven Ca$^{2+}$-specific binding site of a chelator such as BAPTA. Attachment of the BAPTA moiety to the central 9-position of the xanthene would preserve the symmetry of the fluorophore. Such symmetry is desirable because nearly all long-wavelength dyes that are highly fluorescent in water have highly symmetrical polymethine chromophores, whereas asymmetrical chromophores such as merocyanines and rhodols are generally poorly fluorescent in water (see ref. 9).

Classical rhodamines and fluoresceins (see FIG. 1A) are prepared from m-dialkylaminophenols or resorcinols condensed with phthalic anhydrides under harsh conditions. Mixtures of isomers, which are difficult to separate, are generated when the phthalic anhydride bears nonequivalent substituents, as would be required for the BAPTA moiety to be attached to the 9-position. Also, an extra carboxyl would be left adjacent to the junction of the xanthene and phthalein rings. This carboxyl might be undesirable for our purposes because it would interfere sterically with the conjugation between the xanthene system and the phthalein ring. If this conjugation were reduced too much, the fluorophore might become insulated from the chelating site and no longer signal Ca$^{2+}$ binding. Synthetic routes were therefore devised to avoid phthalic anhydrides and the generation of this extra carboxyl.

The synthesis of the new class of calcium specific fluorescent indicator dyes is illustrated in the detailed synthesis of compounds rhod-1, fluo-1, rhod-2, fluo-2, and fluo-3 (see the section labeled: Compound Synthesis). In making these illustrated compounds the BAPTA moiety was activated either by an extra hydroxy substituent as in rhod-1 and fluo-1, or by formation of an organolithium derivative as in rhod-2, fluo-2, and fluo-3, then coupled with various 9-xanthones.

The illustrated compounds all have simple linkages and a simple xanthene fluorophore joined to the "parental" calcium$^{2+}$ chelating moiety. Those skilled in the art will recognize that other forms of these new calcium specific fluorescent dyes, including those where the two 2-bis(carboxymethyl) aminophenoxy groups on the chelator moiety are joined by bulky or "cyclic" linkages, plus those having two xanthene fluorophores attached, can be prepared by skilled artisans, without undue experimentation, by using related synthetic methods and starting materials. For example, compounds with two identical fluorophores are just as easily prepared as those in the specific examples. The synthesis of dyes with W=OH in Formula 2 would begin with reaction of 2 moles of 2-nitro-4-benzyloxyphenol with 1,2-dibromoethane. Reduction of the nitro groups, alkylation of the resulting amino groups with ethyl bromoacetate, and hydrogenolysis of the benzyl groups yields 1,2-bis(2-bis(ethoxycarbonylmethyl)amino-4-hydroxyphenoxy)ethane, the symmetrical analog of Compound I. This can be coupled to 2 moles of 3,6-bis(dimethylamino)xanthone or 3,6-di(benzyloxy)xanthone then deprotected, in analogy to the preparations of rhod-1 and fluo-1, to give dyes of Formula 2 with W=OH.

For dyes of Formula 2 with W=H, 1,2-bis(2-aminophenoxy)ethane, whose synthesis is detailed in ref. 19, would be alkylated with t-butyl bromoacetate as in the preparation of Compound VI. This ester would be brominated then coupled via an organolithium intermediate to 3,6-disubstituted xanthones exactly as in the syntheses of rhod-2, fluo 2, and fluo-3, except that because each symmetrical intermediate has two reactive sites instead of one, double quantities of the other reactants would be employed.

Synthesis of compounds where E$^1$ and/or E$^2$ are different from H can be accomplished by using compounds 4A-4G. (See the Compound Synthesis section of this disclosure.) Any of these diamines could be alkylated with t-butyl bromoacetate, brominated, and coupled to a 3,6-disubstituted xanthone, all in precise analogy to the syntheses of rhod-2, fluo-2, or fluo-3, resulting in dyes of Formula 1 with E$^1$ and E$^2$ different from H. Here, too, the symmetrical derivatives of Formula 2 would be equally easy to make, using 1,2-cyclohexanediols or 2,3-butanediol or 3,4-tetrahydrofurandiol with sodium hydride and >2 moles of 2-fluoronitrobenzene to form the symmetrical nitro ethers, followed by reduction of the nitro groups, alkylation of the amino groups with t-butyl bromoacetate, bromination, and organolithium coupling to 3,6-disubstituted xanthones just as already described.

Variations on the tricyclic chromophore in the Q, Z, and Y groups are well known in the literature and would be prepared from the corresponding 9-xanthones, 9-thioxanthones, 9-acridones, 9-anthrones, 9,10-anthraquinones, and 9-fluorenones.

The most obvious difference between the present chelators and the previous tetracarboxylate Ca$^{2+}$ chelators is in their wavelengths of fluorescence excitation and emission. The new indicators' similarity to fluoresceins and rhodamines make them optically compatible with almost any fluorometer, fluorescence microscope, or flow cytometer already used for immunofluorescence detection. The fluorescein analogs fluo-1, -2, and -3 can be excited by incandescent illumination or the prominent 488 nm line of an argon and ion laser. The rhodamine analogs rhod-1 rhod-2 are suited to incandescent illumination, the 531 nm line of a krypton-ion laser, or the 546 nm line of a mercury arc. By contrast, the earlier dyes quin-2 and fura-2 are best excited at 340-350 or 380-390 nm from a xenon lamp. Indo-1 does best with 350-360 nm from a xenon arc or the low-power UV lines of argon or krypton lasers. Optical elements for these UV wavelengths are preferably reflective or are made from quartz, glasses with enhanced UV transmission, or very thin ordinary glass. Plastics or thick (>1 mm) ordinary glass elements generally give too much absorbance or autofluorescence or both. By contrast, even these cheap optical materials are compatible with blue or green excitation. Visible wavelengths make beam alignment easier, are less likely to excite significant tissue autofluorescence or to damage cells, and do not photolyze "caged" nucleotides or "caged" calcium. Therefore, the new dyes were able (results not shown) to calibrate the [$Ca^{2+}$] increases produced by UV photolysis of nitr-5 or nitr-7, whereas with fura-2 the excitation wavelengths began to photolyze the "caged" calcium and were vulnerable to inner filtering due to the high UV absorbance of the photolysis end product.

Whereas fura-2 and indo-1 were clearly much more intensely fluorescent than quin-2, enabling measurements with much less added dye and $Ca^{2+}$ buffering, comparison of the brightness of the new dyes with that of fura-2 and indo-1 is more complex of the different operating wavelengths. The simplest measure of the intrinsic brightness of a fluorophore is the product of its emission quantum efficiency and its extinction coefficient at the appropriate excitation wavelength (see FIG. 6). At the present time, extinction coefficients are known only for fluo-3, though one may estimate the values for the other indicators from purified model xanthene dyes ($9-10 \times 10^4$ $M^{-1}$ $cm^{-1}$). For fluo-3, the quantum efficiency × extinction coefficient ranges from $3 \times 10^3$ to $1.5 \times 10^4$ $M^{-1}$ $cm^{-1}$ for $Ca^{2+}$ values from $10^{-7}$ M up to saturation, slightly less than the corresponding values for fura-2 excited at 340 nm, $5 \times 10^3$ to $1.6 \times 10^4$ $M^{-1}$ $cm^{-1}$ (see FIG. 6). However, it is easier to generate higher excitation intensities at longer wavelengths, and autofluorescence will be lower, so the actual concentrations of dye needed to overcome dark current and autofluorescence may be fairly similar for the two families. On the other hand, the relatively small separation between excitation and emission peaks of the new dyes makes more stringent demands on monochromators and filters to exclude scattered light.

The $Ca^{2+}$ affinities of the new dyes are two to ten-fold weaker than those of their UV-excited predecessors. This decrease improves resolution of micromolar and higher levels of [$Ca^{2+}$]$_i$, surprisingly without sacrificing resolution of low [$Ca^{2+}$]$_i$ values, at which the large change in fluorescence upon binding $Ca^{2+}$ makes up for the decrease in percentage bound. Thus for fluo-3, just 11 nM [$Ca^{2+}$] gives double the fluorescence at zero [$Ca^{2+}$], due to 2.5% conversion to a $Ca^{2+}$ complex that is forty-fold brighter than the free dye. FIG. 6, which compares curves of normalized intensity vs. log [$Ca^{2+}$] for fluo-3, rhod-2, quin-2, fura-2, and indo-1, emphasizes the ability of fluo-3 to respond sensitively to both low and high [$Ca^{2+}$] values.

The most disappointing feature of the new dyes is the small or negligible shift to absorbance, excitation, or emission wavelengths upon $Ca^{2+}$ binding. We had hoped that $Ca^{2+}$ binding would cause a bathochromic shift by removing electron density previously in conjugation with the 9-position of the xanthene chromophore. Numerous di- and triphenylmethane dyes and bridged heterocyclic analogs are known to show blue and red shifts respectively upon electron donation and withdrawal from the corresponding positions in their chromophores (see ref. 19). One obvious way to rationalize the lack of shift in the present dyes is to postulate severe steric hindrance between the rigidly planar xanthene chromophore and the benzene ring of BAPTA. If the two systems were twisted out of coplanarity, $Ca^{2+}$ binding and immobilization of the lone pair on the amino group would be insulated from the xanthene. We do not know why the $Ca^{2+}$ binding affects the quantum efficiency so dramatically. Perhaps if the amino group is free, the excited state includes a significant contribution from a resonance form with increased bond orders from amino nitrogen to benzene ring and from that to the xanthene. Such increased double-bond character would demand coplanarity, which would conflict with the steric hindrance and result in radiationless deactivation.

Because $Ca^{2+}$ hardly shifts the new dyes' wavelengths, there are not any wavelength pairs in either excitation or emission that are suitable for fluorescence ratioing. Ratioing is extremely valuable with single cells because it cancels out variations in dye concentration and path length. Without ratioing, one cannot convert intensity into $Ca^{2+}$ levels unless the dye concentration, path length, and instrumental sensitivity are either 1) precisely known, or 2) can be held constant while the dye is titrated to known [$Ca^{2+}$] values. The first condition is readily satisfied in extracellular medium in a cuvet, or with somewhat greater difficulty in cells that can be internally perfused with known dye concentrations and whose dimensions can be measured microscopically. The second option can be achieved in suspensions of disaggregated cells by lysing the cells and titrating the supernatant. The alternative of using a Ca ionphore to raise [$Ca^{2+}$]$_i$ in non-perfused single cells is likely to be more difficult with the new dyes than with fura-2 or indo-1. However, if one is content with just a qualitative uncalibrated index of [$Ca^{2+}$]$_i$ changes, the new dyes are highly sensitive (see FIG. 6) without the complexity of alternating wavelengths.

In most applications, fluo-3 will generally be preferable over fluo-1 and fluo-2 because of its lesser sensitivity to pH and its larger fluorescence enhancement on binding $Ca^{2+}$.

Without further elaboration, it is believed that one of ordinary skill in the art can, using the preceding description, utilize the present invention to its fullest extent. The following experimental section and the examples serve to further illustrate how to make and how to use the new dyes of the present invention. They are included for illustrative purposes only, and therefore should not be construed as being limitative in any way of the appended claims.

EXPERIMENTAL PROCEDURES

Examples of the synthetic routes than can be used to produce the new dyes of the present invention are outlined in FIGS. 2 and 3. Full descriptions of the reaction conditions are described below under the section entitled Compound Synthesis. Optical spectra were measured as described by Grynkiewicz, et al. (1985). (See ref. 9.) Quantum efficiencies of fluorescence were obtained (see ref. 10) by comparing the integral of the corrected emission spectrum of the test sample with that of a solution of rhodamine B in ethanol, quantum efficiency assumed to be 0.97 (see ref. 11), or fluorescein in 0.1 M NaOH, quantum efficiency 0.91 (see ref. 10). The concentration of the reference dye was adjusted to match the absorbance of the test sample at the wavelength of excitation.

For measurement of $Ca^{2+}$ dissociation constants at pH 7.0-7.5, free [$Ca^{2+}$] levels were controlled by $Ca^{2+}$/EGTA, $Ca^{2+}$/HEEDTA and $Ca^{2+}$/NTA buffers (see ref. 12) The apparent dissociation constant for the $Ca^{2+}$ EGTA complex was taken as 327 nM at pH 7.03 in 100 mM KCl, 20° C. The logarithms of the apparent dissociation constants for the $Ca^{2+}$ HEEDTA and $Ca^{2+}$ NTA complexes were calculated to be 1.70 - pH and 3.41 - pH, respectively, at room temperature in 0.1 M KCl. To test the pH dependence of the apparent $Ca^{2+}$-dissociation constant of fluo-3 (see FIG. 4), it was necessary to vary pH from 5.6 to 8 while maintaining constant free $Ca^{2+}$. EGTA, HEEDTA, and NTA are too pH-dependent to cover this pH range, so dibromo-BAPTA (chelator 2c of ref 13) was used instead. Because the highest $pK_a$ of this chelator is 5.6, the effective $Ca^{2+}$ affinity is only slightly pH-dependent from pH 5.6 upwards. To compensate for that small dependence, the pH titration was started from pH 5.6 with the appropriate amount of $Ca^{2+}$ in the buffer. Then, at each higher pH, the appropriate small addition of $CaCl_2$ was made to compensate for the increase in the effective $Ca^{2+}$ affinity of the dibromo-BAPTA.

Free [Mg2+] was controlled by $Mg^{2+}$/EGTA buffers assuming an apparent dissociation constant for the $Mg^{2+}$/EGTA complex (including its monoprotonated form) of 6 mM at pH 7.60, 0.12 M ionic strength, 20°, as calculated from the data of Martell & Smith (see ref. 12).

ORGANIC SYNTHESES

In preparing the illustrated compounds of the present invention, two key intermediates and two distinct routes were employed in the synthesis of these new compounds. The first route (see FIG. 2) was based on Compound I, a BAPTA derivative with an extra hydroxyl group meta to the tertiary amino group on one ring, prepared by debenzylation of compound XXIV of Grynkiewicz, et al. (see ref. 2). The added phenolic —OH activated the ring sufficiently to permit electrophilic substitution by a 9-xanthone (II or IV), itself activated (see ref. 14) by $(COCl)_2$ or $POCl_3$. 3,6-dimethylaminoxanthone (II), prepared following reference 15, gave after saponification a rhodamine analog, rhod-1, while 3,6-dihydroxyxanthone (see ref. 16) with the hydroxy groups protected as benzyl ethers (IV) gave a fluorescein analog, fluo-1. Attempts to couple xanthones with BAPTA lacking the extra phenolic —OH failed. The second route (See FIG. 3) was therefore devised to provide an alternative and stronger form of activation of the BAPTA nucleus via an organolithium intermediate. Though organolithium reagents normally attack nearly all protected forms of carboxylates, we found, in agreement with Parham (reference 17), that t-butyl esters were resistant enough below $-150°$ to allow lithium-bromine exchange. The lithiation required six equivalents of tertiary butyllithium (t-BuLi) to go to completion, four of which were presumably used to enolize the four ester carbonyls, one to supply the lithium going onto the aryl ring, and one to destroy the t-butyl bromide formed. Once formed, the p-lithio-BAPTA (VIII) was treated in situ with 3,6-bis(dimethylamino)xanthone (II) to give rhod-2, or with 3,6-dihydroxyxanthone (X, protected with t-butyldimethylsilyl groups) to give the fluorescein analog fluo-2, or with 2,7-dichloro-3,6-dihydroxyxanthone (see ref. 18) (XII, likewise protected) to give fluo-3. The free dyes were obtained by removing the protecting groups with boron trifluoride in acetic acid.

COMPOUND SYNTHESIS

Thin-layer chromatography (TLC) was carried out on precoated silica gel (60F-254, E. Merck) or reverse phase (RP-18 F-254s, E. Merck) plates. For column chromatography, silica gel 60(230–400 mesh, E. Merck) was used. Centrifugal chromatography was performed on 1 mm silica layers in a "chromatotron" (Harrison Research, Palo Alto, Calif.).

Proton NMR spectra were recorded on Varian EM-390 at 90 MHz, UCB 200 MHz, and Bruker AM500 MHz spectrometers. Peaks are reported below in the following format: NMR (solvent, operating frequency): chemical shift delta in ppm from tetramethylsilane, multiplicity (s=singlet, d=doublet, dd=doublet of doublets, t=triplet, q=quartet, m=multiplet, br=broad), spin-spin coupling constant if appropriate, integrated number of protons; sometimes several adjacent peaks are too close for their integral to be separated, in which case only the total integral for a cluster is stated.

COMPOUNDS

Compound I 1-(2-Bis(ethoxycarbonylmethyl) amino-4-benzyloxyphenoxy)-2-(2-bis(ethoxy-carbonylmethyl)amino-5-methylphenoxy)ethane, compound XXIV of Grynkiewicz, et al. (see ref. 2), 1 g, was dissolved in acetic acid (15 ml) and hydrogenated at atmospheric pressure with 5% palladium on charcoal. After complete uptake of hydrogen (overnight required), the catalyst was filtered off and the filtrate evaporated to dryness. Trituration of the product with toluene gave a cream-colored solid in nearly quantitative yield. M.p. 82°–84°. NMR ($CDCl_3$, 90 MHz) delta 1.10, t, 12H;

2.20, s, 3H; 4.00, s+q, 16 H; 4.85, s, 4H; 6.45, s, 1H; 6.60, dd, 3H; 7.30, m, 3H.

Compound I+II→III

The phenol VI (120 mg, 0.2 mmole) was dissolved in dry chloroform (2 ml). 3,6-dimethylaminoxanthone, prepared following Ehrlich and Benda (see ref. 15) (60 mg, 0.21 mmole), converted to the chlorocarbonium ion by stirring with oxalyl chloride (see ref. 14), was added in dry chloroform. After stirring at room temperature overnight, the reaction mixture was diluted with more chloroform and washed with sodium bicarbonate, and then evaporated to give a pinkish-purplish gum. This residue was purified by chromatography on silica gel to give a pink-purplish solid (56 mg, 32%). NMR ($CDCl_3$, 90 MHz) delta 1.20, t, 12H; 2.05, s, 3H; 3.15, s, 12H; 4.00–4.30, 2s+q, 20H; 6.25, s, br, 1H; 6.50–6.80, m, 8H; 7.20, d, 12 Hz, 1H; 7.60, d, 12Hz, 1H.

Compound III→rhod-1

The ester XIV (4 m9) was dissolved in methanol (500 microliters). Dioxane (200 microliters) and aqueous KOH (1 M) (200 microliters) were added. The reaction mixture was stirred at room temperature and monitored by thin layer chromatography until all the ester had hydrolyzed. The reaction mixture was then evaporated to dryness and redissolved in water. Acidification to pH 2 gave a dark purplish solid (rhod-1).

Compound I+IV→V→fluo-1

The phenol I (40 mg, 0.06 mmole) and 3,6-di(benzyloxy)xanthone (IV, prepared by benzylation of 3,6-dihydroxy-9-xanthone (see ref. 16)) were dissolved in $POCl_3$ and heated at 100° C. for two hours. The reaction mixture containing V was evaporated in vacuo, taken into acetic acid and a little formic acid was added.

The mixture was heated under reflux overnight to remove the protecting groups and evaporated in vacuo. The residue was taken into basic buffer and washed with ethyl acetate three times. Acidification with hydrochloric acid to pH 2 gave fluo-1 as a reddish-brown solid.

Compound VI 1-(2-Aminophenoxy)-2-(2- amino-5-methylphenoxy)ethane, Compound V of Grynkiewicz, et al. (see ref. 2) (1.032 g, 4 mmole), 1,8-bis(dimethylamino)naphthalene (4.4 g, 20 mmole), anhydrous sodium iodide (200 mg, 1.2 mmole), tert-butyl bromoacetate (4.680 g, 24 mmole) and acetonitrile (10 ml) were stirred with heating under reflux for 18 hours. The cooled mixture was diluted with toluene and filtered. The filtrate was extracted with phosphate buffer at pH 2 until the 1,8-bis(dimethylamino)naphthalene was removed. The residue recrystallized from ethanol gave white needles (2.4 g, 86% yield). M.p. 118°–119.5°. NMR (CDCl$_3$, 90 MHz) delta 1.40, s, 36H; 2.25, s, 3H; 4.00, s, 4H; 4.05, s, 4H; 4.30, s, 4H; 6.85, m, 3H; 6.90, s, 4H.

Compound VI→VII

The ester VI (2.16 g, 3 mmole) was dissolved in 30 ml dichloromethane and cooled to −78°. Pyridine (355 mg, 4.5 mmole) was added and the mixture was stirred while bromine (572 mg, 3.6 mmole) in dichloromethane (5 ml) was added. The mixture was allowed to warm up to room temperature and then evaporated in vacuo. The residue was taken into chloroform and washed with water, sodium bicarbonate solution, and then brine. The organic layer was dried and the residue crystallized with ethanol (2.01 g, 83%). M.p. 129°–131° C. NMR (CDCl$_3$, 90 MHz) delta 1.42, s, 36H; 2.25, s, 3H; 4.00, s, 8H; 4.35, s, 4H; 6 75, d+m, 3H; 6.85-7.05 (s+m), 3H.

Compound VII→VIII; VIII+II→IX

The bromide VII—(80 mg, 0.1 mmole) was dissolved in 2-methyl-tetrahydrofuran (2 ml) and stirred at −150° C. in a liquid nitrogen-isopentane bath. Tertiary butyllithium (6 equivalents) in hexane (1.7 M, Aldrich Chemical Co.) was added and the metallation monitored by thin layer chromatography of small samples quenched into water. When metallation was complete, the samples showed only the dehalogenated ester VI instead of the bromo compound VII. 3,6-bis(dimethylamino)xanth-9-one (II), (43 mg, 0.15 mmole) (see ref. 15), dissolved in tetrahydrofuran was added dropwise to the reaction mixture. Stirring was continued for another 30 minutes; the bath temperature was not allowed to rise above −130° C. The reaction mixture was quenched with water in tetrahydrofuran and then allowed to warm up to room temperature. It was then extracted twice with ethyl acetate. The combined organic extracts were backwashed with brine and evaporated to dryness. The residue was then stirred with acetic acid to convert all the leuco-base into the dye. Evaporation of the acetic acid in vacuo left a gummy residue which was purified by column chromatography on silica gel (25 mg, 25% yield). NMR (CDCl$_3$, 500 MHz) delta 1.38, s, 18H; 1.50, s, 18H; 2.30, s, 3H; 3.35, s, 12H; 3.90, s, 4H; 4.20, s, 4H; 4.40, s, 4H; 6.70-6.90, m, 9H; 7.55, d, 1H; 8.15, d, 1H.

Compound IX→rhod-2

The ester IX (4 mg) was dissolved in acetic acid (500 microliters) and BF$_3$ etherate (50 microliters) was added. The resulting solution was stirred at room temperature overnight. The solution was then evaporated in vacuo at 35° C. and then basified with buffer. The basic solution was washed three times with ethyl acetate and then acidified with hydrochloric acid to pH 2 to give rhod-2 as dark purplish solid.

Compound X 3,6-dihydroxyxanth-9-one (see ref. 16), 115 mg, 0.5 mmole, was dissolved in dry dimethylformamide. Imidazole (340 mg, 5 mmole) and t-butyldimethylchlorosilane (450 mg, 3 mmole) were added. After stirring at room temperature for 2 h, the mixture was diluted with toluene, washed extensively with water and dried over MgSO$_4$. Evaporation in vacuo gave a white solid, which was recrystallized from ethanol to give 185 mg (77%) of white needles. M.p. 151–154°. NMR (CDCl$_3$, 90 MHz) delta 0.20, s, 12H; 0.090, s, 18H; 6.80, m, 4H; 8.15, d, 9Hz, 2H.

Compound VIII+X→XI

The bromide VII (80 mg, 0.1 mmole) was converted to organolithium intermediate VIII and reacted with X, 3,6-bis(t-butyldimethylsilyloxy)xanthone (100 mg, 0.20 mmole) in analogy to the preparation of IX described above. The ester XI was obtained as a reddish-brown solid (45 mg, 48%). NMR (CDCl$_3$, 500 MHz) delta 1.40, s, 18H; 1.50, s, 18H; 2.30, s, 3H; 3.98, s, 4H; 4.20, s, 4H; 4.37, s, 4H; 6.70, d+s, 2H; 6.95, m, 9H; 7.40, d, 1H.

Compound→fluo-2

The t-butyl groups in XI (5 mg) were removed with BF$_3$ etherate in acetic acid just as in the preparation of rhod-2 above, giving fluo-2 as a reddish-brown solid.

Compound XII 2,7-dichloro-3,6-dihydroxyxanth-9-one (450 mg, 1.5 mmole), obtained following Kurduker and Subba Rao (see ref. 18), was derivatized with imidazole (1.02 g, 15 mmole) and t-butyldimethylchlorosilane (1.35 g, 9 mmole) in dimethylformamide, just as described for X above. The bis(t-butyldimethylsilyl) ether XII was recrystallized from ethanol to give 660 mg (78%) white needles. M.p. 161°–164°. NMR (CDCl$_3$, 90 MHz) delta 0.15, s, 12H; 0.95, s, 18H; 6.20, s, 2H; 7.35, s, 2H.

Compound VIII+XII→XIII

The bromide II (80 mg, 0.1 mmole) was converted to the organolithium derivative VIII, reacted with XII (90 mg, 0.17 mmole), and worked up as described above for the preparation of IX. XIII was obtained as a red solid (55 mg, 55% yield). It was further purified by centrifugal chromatography in silica eluted with hexane-ethyl acetate-acetic acid 0:50:1 (v/v) followed by crystallization from di-isopropyl ether. M.p. 188°–192° with decomposition. NMR (CDCl$_3$, 200 MHz) delta 1.40, s, 18H; 1.50, s, 18H; 2.30, s, 3H; 3.85, s, 4H; 4.05, s, 4H; 4.42, s, 4H; 7.35, s, 1H; 6.75-7.20, m, 9H. The visible spectrum in ethanol solution containing a trace of triethylamine showed a main peak at 520 nm (extinction coefficient = $1.02 \times 10^5$ M$^{-1}$ cm$^{-1}$) with a shoulder at 486 nm extinction coefficient = $2.91 \times 10^4$).

Compound XIII→fluo-3

The t-butyl groups in ester XIII (2 mg) were removed with BF$_3$ etherate in acetic acid as described already for rhod-2. Fluo-3 was obtained as a reddish-brown solid. For determination of the extinction coefficient, the number of micromoles of dye was based on the weight of the starting ester XIII rather than of the free acid, which contained some inert residues from the deesterification reagents.

OTHER COMPOUNDS

The following section details synthesis of additional compounds useful in making the new fluorescent dyes of the present invention.

Compound 1A 2A (5.86 g, 25 mmole) dissolved in dry THF (25 ml) at −10° C. was added dropwise with stirring to a solution of lithium trisiamylborohydride [reagent 6] (30 mmole) in THF (30 ml) at −78° C. under a $N_2$ atmosphere. After 2 h, the red reaction mixture was allowed to warm up to room temperature (1 h), quenched with $H_2O$ (4ml) and EtOH (15 mL), made alkaline with aqueous KOH (6 ml, 10M), and oxidized by cautious addition of 30% aq. $H_2O_2$ (15 ml) with cooling. After saturating with $K_2CO_3$, the aqueous layer was separated and washed with $Et_2O$:THF (1:1, 2×10 ml), The combined organic extracts were dried ($MgSO_4$), evaporated to dryness and the product distilled bulb-to-bulb at 180°–200° C. at 0.1 mm Hg to yield Ia as an orange oil (4.55 g, 77%).

$^1$H NMR delta 1.9 (br m, 6H, —$(CH_2)_3$—) 2.40 (s,3H, $CH_3$) 3.05 (br s, 1H, OH), 4.20, 4.66 (2m, 2H CH) 6.82 (d, 1H, J=8Hz, H-4), 6.90 (s, 1H, H-6) 7.76 (d, 1H, J=8Hz, H-3).

Compound 1B

Trans-2′ (5-methyl-2-nitrophenoxy) cyclopentanol was prepared as follows:

Cyclopentene oxide [reagent 2] (8.73 ml, 0.1 mole), 5-methyl-2-nitrophenol (15.3 g, 0.1 mole) [reagent 1] and potassium 5-methyl-2-nitrophenoxide (1.91 g, 0.01 mole) were dissolved in dry DMF (5 ml) and refluxed for 20 h under argon. The cooled reaction mixture was diluted with aq. NaOH solution (100 ml 1M) and extracted with toluene (three 50 ml portions). The combined extracts were washed with $H_2O$ (3×50 ml), dried ($Na_2SO_4$), toluene removed by evaporation and the product [compound 1B] collected to give 17.0g (72%) of an orange oil which crystallized on cooling. M.p 42°–44°.

$^1$H NMR delta 1.9(br m, 6H, cyclopentyl $CH_2$—), 2.40 (s, 3H, $CH_3$), 4.40 (br m, 1H, —CH—OH), 4.65 (m, 1H, —CH—OAr), 6.80(d, 1H, J=8Hz, H-64), 6.93 (s, 1H, H-6), 7.67 (d, 1H, J=8Hz, H-3)

TLC in a system which separated the cis and transisomers 1A and 1B respectively, indicated complete conversion to the cis-isomer.

Compound 1C

In analogy to the above preparation of 1A, 2C was reduced to 1C, a dark orange oil (54% yield) after chromatography on $SiO_2$ in ethyl acetate-hexane. $^1$H NMR delta 1.68 (br m's, 8H, —$(CH_2)_4$—), 2.40 (s, 3H, $CH_3$), 2.70 (br d, 1H, OH), 3.83 (br m, 1H, CH—), 4.53 (m, 1H, CH—OAr), 6.80 (d, 1H J=8Hz H-4), 6.90 (s, 1H, H-6) 7.76 (d, 1H, J=8Hz H-3).

Compound 1D

Compound 1D was synthesized by the same method as 1B but using cyclohexene oxide [reagent 3] instead of cyclopentene oxide. Recrystallization from hexane gave yellow crystals, yield 56%. M.p. 55°–57°. $^1$H NMR delta 1.50, 1.78, 2.1 (br m, 8H, cyclohexyl), 2.40 (s, 3H, $CH_3$), 3.30 (s, br, 1H, OH), 3.73 (m, 1H, —CH—OH), 4.05 (m, 1H, —CH—OAr), 6.78 (d, 1H, J=8Hz, H-4) 6.90 (s, 1H,H-6), 7, 67 (d, 1H, J=8Hz, H-3).

Compound 1E

Compound 1E was synthesized by the same method as 1B but using trans-2,3-epoxybutane [reagent 4] instead of cyclopentene oxide. The resulting oil (16% yield of 1E) was used without further purification.

$^1$H NMR delta 1.20, 1.30 (2d, 6H, J=5Hz, butyl$CH_3$), 2.40 (s, 3H, Ar—$CH_3$), 2.72 (s, 1H, —OH), 4.00, 4.53 (2m, 2H, J=3Hz, —CH—), 6.85 (d, 2H, J=8Hz, H-4), 6.95 (s, 1H, H-6), 7.80 (d, 2H, J=8Hz, H-3).

Compound 1F

Similarly to the preparation of compound 1G, addition of NaH (4 mmole) to a solution of (R,R)-(-)-2,3-butanediol [reagent 9] (5 mmole) and 2-fluoronitrobenzene [reagent 7] (4 mmol) in dry N-methylpyrrolidinone (2.5 ml), quenching with $H_2O$ after 30 min., and extraction into ethyl acetate gave a mixture of the mono and di-substituted products which were separated on $SiO_2$ by eluting with ethylacetate-hexane to give a yellow oil, 1F (45%) and white solid (14%) respectively.

Compound 1G

Cis-3′-(2-nitrophenoxy)tetrahydrofuran-4′-ol was prepared as follows:

NaH (42 mg 57% suspension in oil, 1 mmole) was added portionwise with stirring to a solution of cis-tetrahydrofuran-3,4-diol [reagent 8] (0.21 g, 2 mmole) and 2-fluoronitrobenzene [reagent 7] (105 microliters, 1 mmole) in dry DMF (1 ml). Thirty minutes after the final addition, the reaction mixture was diluted with $H_2O$ (15 ml) and cooled on ice for at least 30 min. The solid precipitate of the diarylated byproduct was filtered off, the filtrate extracted with toluene (3×5 ml) and combined extracts dried ($Na_2SO_4$), and evaporated to dryness to yield the product, (1G) as a yellow oil that crystallized on trituration with isopropyl ether, yield 111 mg. M.p. 59°–61°. TLC (5% MeOH—$CHCl_3$) showed less than 5% disubstituted by-product. The product was used without further purification.

$^1$H NMR delta 3.13 (d, 1H, OH), 3.4-4.2 (m's, 4H, —$CH_2OCH_2$—), 4.45, 5.80 (2m, 2H, CH), 6.90-8.0 (m, 4H, aromatic).

Compound 2A 2′-(5-methyl-2-nitrophenoxy) cyclopentanone was prepared as follows:

Compound 1B (8.3g, 35 mmole) dissolved in $CH_2Cl_2$ (10 ml) was added in one portion to a stirred suspension of pyridinium chlorochromate [reagent 5] (11.3 g, 55 mmole) in $CH_2Cl_2$ (70 ml) and stirred at room temperature for 16 h. The reaction mixture was diluted with $Et_2O$ (350 ml) and decanted from the dark tar which was washed (3×50ml, with $Et_2O$). The combined extracts were filtered through Celite and evaporated to dryness to yield an oil which crystallized. Recrystallization from MeOH gave 2A as yellow crystals (6.60 g, 80%), M.p 65°–66°.

$^1$H NMR delta 2.10 (m, 6H, —$(CH_2)_3$—), 2.33 (s, 3H, $CH_3$), 4.63 (t, 1H, CH), 6.80 (d, 1H, J=8Hz, H-4), 7.02 (s, 1H, H-6) 7.70 (d, 2H J=8Hz, H-3),

Compound 2C

Oxidation of the cyclohexanol derivative 1D required a six-fold excess of pyridinium chlorochromate and a reaction time of 5 days to give compound 2C (88% yield) as a yellow solid, recrystallized from isopropyl ether. M.p. 125°-8°.

$^1$H NMR delta 1.6-2.6 (m's, 8H, —(CH$_2$)$_4$—), 2.33 (s, 3H, CH$_3$), 4.63 (t, 1H, CH) 6.80 (d, 1H, J=8Hz, H-4), 7.02 (s, 1H, H-6), 7.73 (d, 2H, J=8Hz, H-3).

Compound 3A

Cis-1-(5'-methyl-2'-nitrophenoxy)-2-(2" -nitrophenoxy)cyclopentane was prepared as follows:

NaH (1.05 g, 57% oil suspension, 25 mmole) was added portionwise with stirring and cooling to a solution of 1A (4.27 g, 18 mmole) and 2-fluoronitrobenzene [reagent 7] (2.11 ml, 20 mmole) in dry 1,2-dimethoxyethane (25 ml). After standing at room temperature for 1 h, the reaction mixture was diluted with H$_2$O (100 and extracted with CHCl$_3$ (3×50 ml); the extracts dried and evaporated to dryness to yield the crude product 3A as an oil which crystallized on chilling. Recrystallization from acetone-methanol gave yellow crystals. M.p. 109°-111° yield, 4.8 g (74%).

$^1$H NMR delta 1.7-2.2 (m, 6H, —(CH$_2$)$_3$—), 2.35 (s, 3H, CH$_3$), 4.87 (m, 2H, CH), 6.7-7.8 (m's, 7H, aromatic).

Compounds 3B, C, D and E

Compounds 3B, 3C, 3D and 3E were synthesized from the corresponding alcohols by the same method used to synthesize compound 1A. The yield, physical and spectral properties were as follows:

3B; Orange oil, distilled bulb-to-bulb 230° C. at 0.25 mm Hg (63%)

$^1$H NMR delta 1.6-2.1 (m, 6H, —(CH$_2$)$_3$—), 2.40 (s, 3H, CH$_3$), 4.75 (m, 2H, CH), 6.8-7.8 (m, 7H, aromatic).

3C: Brown oil (SiO$_2$ chromatography, ethylacetate-hexane) yield 74%

$^1$H NMR delta 1.3-2.2 (m's, 8H, —(CH$_2$)$_4$—), 2.37 (s, 3H, CH$_3$), 4.70 (br d, 2H, CH), 6.8-7.8 (m's, 7H aromatic).

3D: Yellow crystals M.p. 86°-90° (60%) (s, 3H, CH$_3$), 4.63 (m, 2H, CH), 6.8-7.8 (m's, 7H, aromatic).

3E: Pale yellow solid M.p. 86° (64%) purified by SiO$_2$ chromatography.

$^1$H NMR delta 1.47 (d, 6H, J=6.5Hz, CH$_3$) 2.42 (s, 3H, Ar—CH$_3$), 4.75 (q, d, 2H, J=6.5, 3Hz, CH), 6.8-8.0 (m, 7H, aromatic).

Compounds 3F and G

As in the synthesis of compounds 3B, C, D and E, compounds 3F and 3G were similarly prepared from alcohols 1F and 1G respectively, but substituting 3-fluoro-4-nitrotoluene [reagent 10] for 2-fluoronitrobenzene. 3F was an orange oil, separated by SiO$_2$ chromatography (ethyl acetate-hexane) yield 45%.

$^1$H NMR delta 1.33 (d, 6H, J=6.5Hz, CH$_3$), 2.40 (s, 3H, Ar—CH$_3$), 4.75 (m, 1H, CH), 6.7-7.8 (m's, 7H, aromatic).

3G was obtained as a pale yellow precipitate on quenching the reaction mixture followed by recrystallization from ethanol. Yield 63% M.p. 145°-148°.

$^1$H NMR delta 2.37 (s, 3H, CH$_3$), 4.21 (m, 4H, —CH$_2$OCH$_2$—), 5.07 (m, 2H, CH) 6.8-7.8 (m's, 7H, aromatic).

Compound 4A

Cis 1-(2-aminophenoxy)-2-(2-amino-5-methylphenoxy)cyclopentane was prepared as follows: 3A (2.0g, 5.58 mmole) was catalytically hydrogenated at room temperature and pressure with 200 mg 5% Pd/C in ethylacetate: 95% aq. EtOH (2:1). Uptake was complete within 1 h and after a further,1 h, the reaction mixture was filtered and evaporated to dryness to yield the product 4A as a pale brown oil which was used in the following reaction without further purification.

$^1$H NMR delta 1.6-2.2 (br m, 6H, —(CH$_2$)$_3$—), 2.18 (s, 3H, CH$_3$), 3.67 (br s, 4H, NH$_2$), 4.63 (m, 2H, CH), 6.4-6.8 (m, 7H, aromatic).

Compounds 4B-G

Similarly to the preparation of compound 4A, nitroethers 3B-G were hydrogenated over Pd/C catalyst in ethyl acetate or ethanol The amine products 4B-G were usually oils which darkened on exposure to air, gave the expected NMR spectra and were used without further purification.

(Compound 4B is: trans 1-(2-aminophenoxy)-2-(2-amino-5-methylphenoxy)cyclopentane;

Compound 4C is: cis 1-(2-aminophenoxy)-2-(2-amino-5-methylphenoxy)cyclohexane;

Compound 4D is: trans 1-(2-aminophenoxy)-2-(2-amino-5-methylphenoxy)cyclohexane;

Compound 4E is: cis 2-(2-aminophenoxy)-3-(2-amino-5-methylphenoxy)butane;

Compound 4F is: trans 2-(2-aminophenoxy)-3-(2-amino-5-methylphenoxy)butane;

Compound 4G is: cis 3-(2-aminophenoxy)-4-(2-amino-5-methylphenoxy)tetrahydrofuran.)

EXAMPLES

Example 1

Absorbance and Fluorescence Properties

The absorbance and fluorescence properties for the new indicators in the presence and absence of Ca$^{2+}$ are shown in Table I. The absorbance spectra were much as one would expect for rhodamine or fluorescein chromophores, though extinction coefficients (not shown) were often low in the dyes as initially isolated. Because fluo-3 appeared to be a very useful indicator compound, extra effort was expended in its purification. Eventually, quite respectable extinction coefficients were obtained, $7.9 \times 10^4$ and $8.3 \times 10^4$ M$^{-1}$ cm$^{-1}$ at 503 and 506 nm, respectively for free and Ca$^{2+}$-bound fluo-3. Ca$^{2+}$ binding was expected to shift the absorbance maxima to longer wavelengths, since it would prevent the BAPTA amino nitrogen from donating electron density to the 9-position of the xanthene. Electron-withdrawal and donation to the central carbon of triphenylmethane dyes are known to shift absorbance peaks to longer and shorter wavelengths, respectively (see ref. 19). Indeed, Ca$^{2+}$ binding caused red shifts, but of very small magnitude, 1-3 nm, and with little change in peak height.

All the new indicator compounds tested showed fluorescence qualitatively similar to rhodamines or fluoresceins as expected. For example, FIG. 4 shows excitation and emission spectra for fluo-3 as a function of free [Ca$^{2+}$] in EGTA buffers. Fluo-3 has a visibly pinkish tinge because its chlorine atoms shift its spectra to wavelengths slightly longer than those of fluo-2, just as 2,7-dichlorofluorescein is bathochromically shifted from fluorescein. Fluorescence intensities were very strongly enhanced by Ca$^{2+}$ binding. Thus the Ca$^{2+}$ complex of fluo-3 fluoresced 35- to 40-fold more brightly than the Ca$^{2+}$-free dye (see FIG. 4). This degree of enhancement is the greatest yet reported for a fluorescent Ca$^{2+}$ indicator. However, Ca$^{2+}$ binding caused little change in the wavelengths of peak excitation or emission, so that these dyes gave no useful change in excitation or emission ratio. Also, even with $Ca^{2+}$ bound, the quantum efficiencies of fluorescence were considerably less than those of true rhodamines or fluoresceins in water (up to 0.9), though comparable with those of model compounds such as 9-phenylfluorone, quantum efficiency 0.21 (see ref. 20), that similarly lack the extra phthalein carboxyl.

Fluo-3 was briefly checked for photochemical stability. In the air-saturated solutions illuminated with a xenon arc filtered only by glass lenses, $Ca^{2+}$-free fluo-3 bleached at about the same rate as ordinary fluorescein anion, whereas the $Ca^{2+}$ complex bleached about half as quickly. Since the biological usability of fluorescein is well established, the photochemical resistance of fluo-3 would seem to be adequate if not outstanding.

Example 2

$Ca^{2+}$-binding constants $Ca^{2+}$ dissociation constants for all the new chelators tested thus far (see Table I) are in the range of 370 nM–2.3 microM at ionic strengths 0.1–0.15. These values are significantly higher than those for the parent compounds BAPTA (110 nM, see ref. 13) and its p-methyl derivative "benz"[2] (79 nM), indicating that the xanthene chromophores are somewhat electron-withdrawing. The positively charged rhodamines are distinctly lower in affinity than the negatively charged fluoresceins, as expected. A hydroxy group on the BAPTA aromatic ring, as in rhod-1 and fluo-1, also lowers the $Ca^{2+}$ affinity more than two-fold compared to the unsubstituted rhod-2 and fluo-2, presumably because a hydroxy group is inductively electron withdrawing when meta to the reaction center, the amino nitrogen. The chlorines added in fluo-3 have very little effect, because they are too far from the chelating site.

Example 3

Cation Selectivity

The fluoresceins fluo-1 and fluo-2 were expected and found to show some pH dependence due to the ability of the phenolic hydroxyl on the xanthese chromophore to accept a proton. For example, the fluorescence of fluo-2 was almost completely quenched as the pH was titrated from pH 7.7 to 4.1 in the absence of $Ca^{2+}$. The titration curve fitted a $pK_a$ of $6.20\pm0.02$ and a ratio of 67 between the brightness of the deprotonated and the protonated species. Because protonation quenches fluorescence, this $pK_a$ is probably on the fluorescein chromophore not the chelator amino group. Protonation of the latter would be expected to act like $Ca^{2+}$ and enhance fluorescence. A $pK_a$ of 6.2 would normally be fairly safely remote from typical cytosolic pH's, but because protonation has such a powerful effect on the fluorescence and is spectrally indistinguishable from a drop in $[Ca^{2+}]$, fluo-2 is too pH-sensitive for general use. This problem was the motivation for the synthesis of a compound like fluo-3, with chloro substituents to increase the acidity of the chromophore. With fluo-3, the $pK_a$ fell to 4.5–4.6 as assessed either by the absorbance spectrum, which was practically $Ca^{2+}$-independent, or by the fluorescence amplitude of the $Ca^{2+}$-complex at saturating (mM) $Ca^{2+}$ levels (top curve, FIG. 5). Because this $pK_a$ was shifted to such a low value, it became possible to detect protonation on an amino nitrogen with a $pK_a$ of about 6.2. This protonation was revealed by a modest increase, maximally 3-fold, of the fluorescence of the $Ca^{2+}$-free dye as the pH was titrated from pH 8 to pH 5 (bottom curve, FIG. 5). Amino protonation is similar to $Ca^{2+}$-binding in that both have negligible effect on the absorbance spectrum yet enhance fluorescence quantum efficiency. Protonation tends to inhibit $Ca^{2+}$-binding, as shown by the two curves at intermediate $[Ca^{2+}]$ in FIG. 5. At a pH of about 6.1–6.2, a given intermediate concentration of $Ca^{2+}$ is about half as effective at enhancing fluorescence as it is at pH ~8, an independent rough confirmation of an amino $pK_a$ near 6.2.

The $Mg^{2+}$ dissociation constant for fluo-3 was found to be 9 mM at 25°, 0.1–0.15 M ionic strength. This value is practically the same as that (8.1 mM) of the parent compound[2] "benz4" lacking the xanthene chromophore. Evidently the electron-withdrawing effect of the xanthene does not affect the $Mg^{2+}$ affinity nearly as much as it reduces the $Ca^{2+}$ affinity. This result can be explained if the $Mg^{2+}$ binds mainly to the half of the chelator that is remote from the chromophore. In confirmation of this hypothesis, $Mg^{2+}$ binding also has relatively little effect on the chelator fluorescence, boosting it only about 1.4-fold, much less than the 40-fold enhancement from $Ca^{2+}$ binding.

TABLE I

| Dye | Fluorescence maxima (nm) with excess Ca | | Quantum efficiencies | | Fluorescence ratio, excess vs. zero Ca | Effective dissociation Constant $K_d$ for $Ca^{2+}$ |
|---|---|---|---|---|---|---|
| | excitation | emission | zero Ca | excess Ca | | |
| rhod-1 | 556 | 578 | .0014 | .021 | 15 | 2.3 microM |
| fluo-1 | 499 | 521 | .0042 | .014 | 3.3 | 0.7 microM |
| rhod-2 | 553 | 576 | .03 | .102 | 3.4 | 1.0 microM |
| fluo-2 | 493 | 518 | .004 | .125 | 31 | 0.37 microM |
| fluo-3 | 506 | 526 | .0051 | .183 | 36–40 | 0.45 microM |

SUMMARY

From the foregoing description, one of ordinary skill in the art can easily ascertain that the present invention provides novel calcium specific fluorescent indicator dyes having visible excitation and emission wavelengths. These novel fluorescent indicator dyes combine at least one tricyclic chromophore with a tetracarboxylate parent $Ca^{2+}$ chelating compound having the octacoordinate pattern of ligand groups characteristic of BAPTA to give a rhodamine-like or fluorescein-like fluorophore. Binding of calcium2+ increases the fluorescence of the new compounds by up to 40-fold The calcium2+ dissociation constants are in the range 0.37–2.3 microM, so that the new indicators give better resolution of high [CA2+] levels than were previously obtainable with predecessor compounds such as quin-2 or fluo-2. The visible excitation wavelengths of the new compounds are more convenient for fluorescence microscopy and flow cytometry than the UV required by previous indicators.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A chemical compound having the general formula:

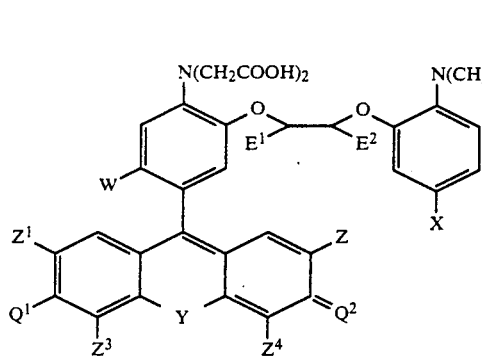

and the pharmaceutically acceptable non-toxic salts and esters thereof wherein:

$E^1$ and $E^2$ are independently H, $CH_3$, $C_2H_5$, $CH_2OH$, COOH, or $CH_2COOH$, or $E^1$ and $E^2$ together are $-(CH_2)_m-V-(CH_2)_n-$ where m and n are independently 1 or 2 and V is selected from the group consisting of $-CH_2-$, $-O-$, $-NH-$, $-NMe-$, $-S-$, and $-S-S-$;

W is H, OH, or COOH;

X is H, Me, COOH, F, Cl, Br, I, or $NO_2$;

Y is $-O-$, $-NMe-$, $-S-$, $-CH_2-$, $-CMe_2-$, $-CF_2-$,

or a direct sigma bond making a five-membered central ring;

$Z^1$, $Z^2$, $Z^3$, and $Z^4$ are independently H, F, Cl, Br, I, or Me, and $Q^1$, $Q^2$ equal $R_1R_2N-$,

or $HO-$, $O=$ or $R_1R_2N-$, $O=$, where $R^1$ and $R_2$ are independently selected from the group consisting of H, Me, and Et; or $Z^1$, $Q^1$, $Z^3$ together are

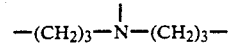

and $Z^2$, $Q^2$, $Z^4$ together are

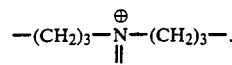

2. The compound of claim 1 wherein said tetraacetic acid esters are alpha-acyloxyalkyl esters.

3. The compound of claim 1 wherein said alpha-acyloxyalkyl esters are acetoxymethyl esters.

4. A chemical compound having the general formula:

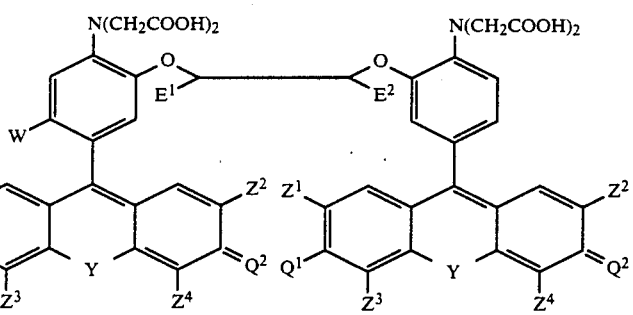

and the pharmaceutically acceptable non-toxic salts and esters thereof wherein:

$E^1$ and $E^2$ are independently H, $CH_3$, $C_2H_5$, $CH_2OH$, COOH, or $CH_2COOH$, or $E^1$ and $E^2$ together are $-(CH_2)_m-V-CH_2)_n-$ where m and n are independently 1 or 2 and V is selected from the group consisting of $-CH_2-$, $-O-$, $-NH-$, $-NMe-$, $-S-$, and $-S-S-$;

W is H, OH, or COOH;

X is H, Me, COOH, F, Cl, Br, I, or $NO_2$;

Y is $-O-$, $-NMe-$, $-S-$, $-CH_2-$, $-CMe_2-$, $-CF_2-$,

or a direct sigma bond making five-membered central ring;

$Z^1$, $Z^2$, $Z^3$, and $Z^4$ are independently H, F, Cl, Br, I, or Me, and $Q^1$, $Q^2$ equal $R_1R_2N-$,

or $HO-$, $O=$ or $R_1R_2N-$, $O=$, where $R^1$ and $R_2$ are independently selected from the group consisting of H, Me, and Et; or $Z^1$, $Q^1$, $Z^3$ together are

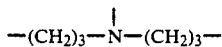

and $Z^2$, $Q^2$, $Z^4$ together are

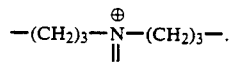

5. The compound of claim 4 wherein said tetraacetic acid esters are alpha-acyloxyalkyl esters.

6. The compound of claim 4 wherein said alpha-acyloxyalkyl esters are acetoxymethyl esters.

7. A fluorescent, calcium binding compound comprised of (9-(6-hydroxy-4-bis(carboxymethyl)amino-3-(2-(2-bis(carboxymethyl)amino-5-methylphenoxy)ethoxy) phenyl)-6-dimethylamino-3H-xanthen-3-ylidene)dimethylammonium and the pharmaceutically acceptable non-toxic salts and esters thereof.

8. A fluorescent, calcium binding compound comprised of (9-(4-bis(carboxymethyl)amino-3-(2-(2-bis(carboxymethyl)amino-5-methylphenoxy)ethoxy)phenyl)-6-dimethylamino-3H-xanthen-3-ylidene)dimethylammonium and the pharmaceutically acceptable non-toxic salts and esters thereof.

9. A fluorescent, calcium binding compound comprised of 9-(6-hydroxy-4-bis(carboxymethyl)amino-3-(2-(2-bis(carboxymethyl)amino-5-methylphenoxy)ethoxy) phenyl)-6-hydroxy-3H-xanthen-3-one and the pharmaceutically acceptable non-toxic salts and esters thereof.

10. A fluorescent, calcium binding compound comprised of 9-(4-bis(carboxymethyl)amino-3-(2-(2-bis(carboxymethyl)amino-5-methylphenoxy)ethoxy)phenyl)-6-hydroxy-3H-xanthen-3-one and the pharmaceutically acceptable non-toxic salts and esters thereof.

11. A fluorescent, calcium binding compound comprised of 9-(4-bis(carboxymethyl)amino-3-(2-(2-bis(carboxymethyl)amino-5-methylphenoxy)ethoxy)phenyl)-2,7-dichloro-6-hydroxy-3H-xanthen-3-one and the pharmaceutically acceptable non-toxic salts and esters thereof.

* * * * *